United States Patent
Chang et al.

(10) Patent No.: US 7,592,451 B2
(45) Date of Patent: Sep. 22, 2009

(54) TREATMENT FOR DIABETES AND OBESITY AS WELL AS METHOD OF SCREENING COMPOUNDS USEFUL FOR SUCH TREATMENTS

(75) Inventors: Young-Tae Chang, New York, NY (US); Fabio Piano, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/471,214

(22) Filed: Jun. 20, 2006

(65) Prior Publication Data

US 2006/0293325 A1  Dec. 28, 2006

Related U.S. Application Data

(60) Provisional application No. 60/693,192, filed on Jun. 23, 2005.

(51) Int. Cl.
C07D 251/54 (2006.01)
C07D 251/52 (2006.01)
C07D 251/50 (2006.01)
C07D 403/04 (2006.01)
C07D 417/04 (2006.01)
A61K 31/53 (2006.01)
A61K 31/5375 (2006.01)
A61P 3/10 (2006.01)

(52) U.S. Cl. .......... 544/197; 544/198; 544/206; 544/207; 544/210; 544/113; 514/245

(58) Field of Classification Search .......... 544/197, 544/198, 206, 207, 210, 113; 514/245, 231.5
See application file for complete search history.

(56) References Cited

U.S. PATENT DOCUMENTS

| | | | |
|---|---|---|---|
| 2,508,323 | A | 5/1950 | Adams et al. |
| 2,885,400 | A | 5/1959 | Schock |
| 3,156,690 | A | 11/1964 | Dexter et al. |
| 4,963,363 | A | 10/1990 | Forssen |
| 5,062,882 | A | 11/1991 | Newton et al. |
| 6,150,360 | A | 11/2000 | Daeyaert et al. |
| 6,150,362 | A | 11/2000 | Henkin et al. |
| 6,207,826 | B1 | 3/2001 | Cooke et al. |
| 6,262,053 | B1 | 7/2001 | Uckun et al. |
| 6,372,729 | B1 | 4/2002 | Daeyaert et al. |
| 7,115,737 | B2 | 10/2006 | Chang |
| 7,163,943 | B2 | 1/2007 | Timmer et al. |
| 2002/0103195 | A1 | 8/2002 | Bonham et al. |
| 2003/0109529 | A1 | 6/2003 | Hacker et al. |
| 2003/0166002 | A1 | 9/2003 | Chang et al. |
| 2004/0122009 | A1 | 6/2004 | Chang et al. |
| 2005/0019831 | A1 | 1/2005 | Chang |

FOREIGN PATENT DOCUMENTS

| | | | |
|---|---|---|---|
| CH | 337019 | | 3/1959 |
| CH | 638376 A5 | | 9/1983 |
| EP | 0933376 A2 | | 8/1999 |
| WO | WO 98/05961 A1 | | 2/1998 |
| WO | WO 98/16508 A2 | | 4/1998 |
| WO | WO 98/46551 A1 | | 10/1998 |
| WO | WO 99/31088 A1 | | 6/1999 |
| WO | WO 01/47897 A1 | | 7/2001 |
| WO | WO-2004/091558 A2 | * | 10/2004 |

OTHER PUBLICATIONS

Promega Literature—GAPDH Assay Kit, pp. 1-2, 1999.*
Carroll et al., Pharmacology & Therapeutics 99, 183-220, 2003.*
Hanover et al., PNAS 102(32), 11266-11271, 2005.*
Harding et al., Cell Metabolism, 2(6), 361-371, 2005.*
Bork et al., "Novel Orthogonal Stategy Toward Solid-Phase Synthesis of 1,3,5-Substituted Triazines," *Organic Letters* 5(2):117-20 (2003).
Bork et al., "Palladium-Catalyzed Cross Coupling Reaction of Resin-Bound Chlorotriazines," *Tetrahedron Letters* 44:6141-44 (2003).
Cecil Textbook of Medicine, edited by Bennet, J.C. and Plum F., 20th Edition, vol. 1, 1004-1010 (1996).
Cocuzza et al., "Use of the Suzuki Reaction for the Synthesis of Aryl-Substituted Heterocycles as Corticotropin-Releasing Hormone (CRH) Antagonists," *Bioorganic & MedicinalChemistry Letters* 9(7):1063-66 (1999).
Cooke et al., "Synthesis of 6-Aryl-2,4-Diamino-Pyrimidines and Triazines using Palladium Catalyzed Suzuki Cross-Coupling Reactions," *Tetrahedron* 57(14):2787-89 (2001).
Crews & Splittgerber, "Chemical Genetics: Exploring and Controlling Cellular Processes with Chemical Probes," *Trends in Biochemical Sciences* 24(8):317-20 (1999).

(Continued)

*Primary Examiner*—Venkataraman Balasubramanian
(74) *Attorney, Agent, or Firm*—Nixon Peabody LLP

(57) ABSTRACT

The present invention relates to a compound having the formula

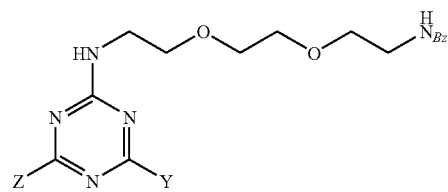

where Z is an amine, phenoxy, or thiol-containing group, and Y is an alkyl-containing amine. Methods of producing such compounds and using them to treat patients with diabetes and obesity are also disclosed. The present invention also relates to treating such conditions with GADPH inhibitors and screening compounds useful for treating such conditions by using GADPH inhibitors. Compounds can also be screened for their effectiveness in modulating diabetes and obesity with a *C. elegans* strain.

18 Claims, 13 Drawing Sheets

OTHER PUBLICATIONS

Ding et al., "A Combinatorial Scaffold Approach Toward Kinase-Directed Heterocycle Libraries," *J. Am. Chem. Society* 124(8):1594-96 (2002).

Filippusson et al., "Design, Synthesis and Evaluation of Biomimetic Affinity Ligands for Elastases," *J. Molecular Recognition* 13:370-81 (2000).

Fivush et al., "AMEBA: An Acid Sensitive Aldehyde Resin for Solid Phase Synthesis," *Tetrahedron Lett.* 38(41):7151-7154 (1997).

Gustafson et al., "Incorporation of Carbohydrates and Peptides Into Large Triazine-Based Screening Libraries using Automated Parallel Synthesis," *Tetrahedron* 54:4051-4065 (1998).

Hajduk et al., "Novel Inhibitors of Methyltransferases for NMR and Parallel Synthesis," *J. Med. Chem.* 42:3852-3859 (1999).

Johnson et al., "Libraries of N-alkylaminoheterocycles from Nucleophilic Aromatic Substitution with Purification by Solid Supported Liquid Extraction," *Tetrahedron* 54:4097-4106 (1998).

Khersonsky et al., "Facilitated Forward Chemical Genetics Using A Tagged Triazine Library and Zebrafish Embryo Screening," *J. Am. Chem. Soc.* 125(39):11804-5 (2003).

Masquelin et al., "Solution and Solid Phase Synthesis of Combinatorial Libraries of Trisubstituted 1,3,5-Triazines," *Heterocycles* 48(12):2489-2505 (1998).

Moon et al., "A Novel Microtubule Destabilizing Entity from Orthogonal Synthesis of a Triazine Library and Zebrafish Embryo Screening," *J. Am. Chem. Soc.* 124(39):11608-9 (2002).

Saito et al., "Synthesis of Biaryls via a Nickel (0)-Catalyzed Cross Coupling Reaction of Chloroarenes with Arylboronic Acids," *J Org. Chem.* 62(23):8024-30 (1997).

Scharn et al., "Spatially Addressed Synthesis of Amino- and Amino-Oxy-Substituted 1,3,5-Triazine Arrays of Polymeric Membranes," *J. Comb. Chem.* 2:361-369 (2000).

Schareina et al., "Combinatorial Libraries with P-functionalized Aminopyridines: Ligands for the Preparation of Efficient C(aryl)-Cl Activation Catalysts," *Angew. Chem. Int. Ed.* 41(9): 1521-23 (2002).

Schreiber, "Chemical Genetics Resulting from a Passion for Synthetic Organic Chemistry," *Bioorganic & Medical Chemistry* 6:1127-52 (1998).

Silen et al., "Screening for Novel Antimicrobials from Encoded Combinatorial Libraries by using a Two-Dimensional Agar Format," *Antimicrobial Agents and Chemotherapy* 42(6):1447-1453 (1998).

Silverman et al., The Organic Chemistry of Drug Design and Drug Action. NewYork:Academic Press, Inc. pp. 19-23 (1992) Stankova et al., "Library Generation through Successive Substitution of Trichlorotriazine," *Molecular Diversity* 2:75-80 (1996) (especially Table 2.2).

Stankova et al., "Library Generation through Successice Substitution of Trichlorotriazine," *Molecular Diversity* 2:75-80 (1996).

Teng et al., "A Strategy for the Generation of Biomimetic Ligands for Affinity Chromatography—Combinatorial Synthesis and Biological Evaluation of an IgG Binding Ligand," *J. Molecular Recognition* 12:67-75 (1999).

Winklmair et al., "Development of a Highly Sensitive Enzyme-Immunoassay for the Determination of Triazine Herbicides," Fresenius J. Anal. Chem. 358:614-22 (1997).

Wood et al., "Past and Future of the Mitotic Spindle as an Oncology Target," *Current Opinion in Pharmacology* 1:370-77 (2001).

Zhang et al., "Orthogonal, Convergent Syntheses of Dendrimers Based on Melamine with One or Two Unique Surface Sites for Manipulation," *J. Am. Chem. Soc.* 123:8914-22 (2001).

* cited by examiner

A.   B.   C.

TG-Bz   F43   E 3

D.   E.   F

|   | A | B | C | D | E | F | G | H | I | J |
|---|---|---|---|---|---|---|---|---|---|---|
| 1 | 471.8 | 595.9 | 507.8 | 537.8 | 457.8 | 477.8 | 483.8 | 443.8 | 478.8 | 505.8 |
| 2 | 525.8 | 649.9 | 561.8 | 591.8 | 511.8 | 531.8 | 537.8 | 497.8 | 532.8 | 559.8 |
| 3 | 522.8 | 646.9 | 558.8 | 588.8 | 508.8 | 528.8 | 534.9 | 494.8 | 529.8 | 556.8 |
| 4 | 522.8 | 646.9 | 558.8 | 588.8 | 508.8 | 528.8 | 534.9 | 494.8 | 529.8 | 556.8 |
| 5 | 539.9 | 663.9 | 575.9 | 605.9 | 525.9 | 545.9 | 551.9 | 511.9 | 546.8 | 573.9 |
| 6 | 521.8 | 645.9 | 557.8 | 587.9 | 507.9 | 527.8 | 533.9 | 493.8 | 528.8 | 555.9 |
| 7 | 487.8 | 611.9 | 523.8 | 553.8 | 473.8 | 493.8 | 499.8 | 459.8 | 494.8 | 521.8 |
| 8 | 487.8 | 611.9 | 523.8 | 553.8 | 473.8 | 493.8 | 499.8 | 459.8 | 494.8 | 521.8 |
| 9 | 556.3 | 680.4 | 592.3 | 622.3 | 542.3 | 562.3 | 568.3 | 528.3 | 563.3 | 590.3 |
| 10 | 485.8 | 609.9 | 521.8 | 551.8 | 471.8 | 491.8 | 497.8 | 457.8 | 492.8 | 519.8 |
| 11 | 527.9 | 652.0 | 563.9 | 593.9 | 513.9 | 533.9 | 539.9 | 499.9 | 534.9 | 561.9 |
| 12 | 527.9 | 652.0 | 563.9 | 593.9 | 513.9 | 533.9 | 539.9 | 499.9 | 534.9 | 561.9 |
| 13 | 513.9 | 637.9 | 549.9 | 579.9 | 499.9 | 519.9 | 525.9 | 485.9 | 520.8 | 547.9 |
| 14 | 541.9 | 666.0 | 577.9 | 607.9 | 527.9 | 547.9 | 553.9 | 513.9 | 548.9 | 575.9 |
| 15 | 499.8 | 623.9 | 535.8 | 565.8 | 485.8 | 505.8 | 511.9 | 471.8 | 506.8 | 533.8 |
| 16 | 581.9 | 706.0 | 617.9 | 647.9 | 567.9 | 587.9 | 593.9 | 553.9 | 588.9 | 615.9 |
| 17 | 581.9 | 706.0 | 617.9 | 647.9 | 567.9 | 587.9 | 593.9 | 553.9 | 588.9 | 615.9 |
| 18 | 501.9 | 625.9 | 537.9 | 567.9 | 487.9 | 507.8 | 513.9 | 473.9 | 508.8 | 535.9 |
| 19 | 539.8 | 663.9 | 575.8 | 605.8 | 525.8 | 545.8 | 551.9 | 511.8 | 546.8 | 573.8 |
| 20 | 539.8 | 663.9 | 575.8 | 605.8 | 525.8 | 545.8 | 551.9 | 511.8 | 546.8 | 573.8 |
| 21 | 539.8 | 663.9 | 575.8 | 605.8 | 525.8 | 545.8 | 551.9 | 511.8 | 546.8 | 573.8 |
| 22 | 501.8 | 625.9 | 537.8 | 567.9 | 487.9 | 507.8 | 513.9 | 473.8 | 508.8 | 535.9 |
| 23 | 473.8 | 597.9 | 509.8 | 539.8 | 459.8 | 479.8 | 485.8 | 445.8 | 480.8 | 507.8 |
| 24 | 551.9 | 675.9 | 587.9 | 617.9 | 537.9 | 557.9 | 563.9 | 523.9 | 558.8 | 585.9 |
| 25 | 551.9 | 675.9 | 587.9 | 617.9 | 537.9 | 557.9 | 563.9 | 523.9 | 558.8 | 585.9 |
| 26 | 565.9 | 690.0 | 601.9 | 631.9 | 551.9 | 571.9 | 577.9 | 537.9 | 572.9 | 599.9 |
| 27 | 535.9 | 659.9 | 571.9 | 601.9 | 521.9 | 541.9 | 547.9 | 507.9 | 542.8 | 569.9 |
| 28 | 535.9 | 659.9 | 571.9 | 601.9 | 521.9 | 541.9 | 547.9 | 507.9 | 542.8 | 569.9 |
| 29 | 527.9 | 652.0 | 563.9 | 593.9 | 513.9 | 533.9 | 539.9 | 499.9 | 534.9 | 561.9 |
| 30 | 527.9 | 652.0 | 563.9 | 593.9 | 513.9 | 533.9 | 539.9 | 499.9 | 534.9 | 561.9 |
| 31 | 501.8 | 625.9 | 537.8 | 567.8 | 487.8 | 507.8 | 513.8 | 473.8 | 508.8 | 535.8 |
| 32 | 621.9 | 746.0 | 657.9 | 687.9 | 607.9 | 627.9 | 633.9 | 593.9 | 628.9 | 655.9 |

FIGURE 5A

| 33 | 543.9 | 668.0 | 579.9 | 609.9 | 529.9 | 549.9 | 556.0 | 515.9 | 550.9 | 577.9 |
|---|---|---|---|---|---|---|---|---|---|---|
| 34 | 535.9 | 659.9 | 571.9 | 601.9 | 521.9 | 541.9 | 547.9 | 507.9 | 542.8 | 569.9 |
| 35 | 499.8 | 623.9 | 535.8 | 565.8 | 485.9 | 505.8 | 511.9 | 471.8 | 506.8 | 533.9 |
| 36 | 565.8 | 689.9 | 601.8 | 631.9 | 551.9 | 571.8 | 577.9 | 537.8 | 572.8 | 599.9 |
| 37 | 485.8 | 609.9 | 521.8 | 551.8 | 471.8 | 491.8 | 497.8 | 457.8 | 492.8 | 519.8 |
| 38 | 547.9 | 671.9 | 583.9 | 613.9 | 533.9 | 553.9 | 559.9 | 519.9 | 554.8 | 581.9 |
| 39 | 566.0 | 690.1 | 602.0 | 632.0 | 552.0 | 572.0 | 578.0 | 538.0 | 573.0 | 600.0 |
| 40 | 580.0 | 704.1 | 616.0 | 646.0 | 566.0 | 586.0 | 592.0 | 552.0 | 587.0 | 614.0 |
| 41 | 551.9 | 675.9 | 587.9 | 617.9 | 537.9 | 557.9 | 563.9 | 523.9 | 558.8 | 585.9 |
| 42 | 604.9 | 729.0 | 640.9 | 670.9 | 590.9 | 610.9 | 617.0 | 576.9 | 611.9 | 638.9 |
| 43 | 567.9 | 691.9 | 603.9 | 633.9 | 553.9 | 573.9 | 579.9 | 539.9 | 574.8 | 601.9 |
| 44 | 503.8 | 627.8 | 539.8 | 569.8 | 489.8 | 509.8 | 515.8 | 475.8 | 510.7 | 537.8 |
| 45 | 531.9 | 655.9 | 567.9 | 597.9 | 517.9 | 537.9 | 543.9 | 503.9 | 538.8 | 565.9 |
| 46 | 517.8 | 641.9 | 553.8 | 583.9 | 503.9 | 523.8 | 529.9 | 489.8 | 524.8 | 551.9 |
| 47 | 517.8 | 641.9 | 553.8 | 583.9 | 503.9 | 523.8 | 529.9 | 489.8 | 524.8 | 551.9 |
| 48 | 475.8 | 599.8 | 511.8 | 541.8 | 461.8 | 481.8 | 487.8 | 447.8 | 482.7 | 509.8 |
| 49 | 488.8 | 612.9 | 524.8 | 554.8 | 474.8 | 494.8 | 500.8 | 460.8 | 495.8 | 522.8 |
| 50 | 474.8 | 598.9 | 510.8 | 540.8 | 460.8 | 480.8 | 486.8 | 446.8 | 481.8 | 508.8 |
| 51 | 500.8 | 624.9 | 536.8 | 566.8 | 486.8 | 506.8 | 512.8 | 472.8 | 507.8 | 534.8 |
| 52 | 503.7 | 627.8 | 539.7 | 569.7 | 489.7 | 509.7 | 515.7 | 475.7 | 510.7 | 537.7 |
| 53 | 545.8 | 669.9 | 581.8 | 611.8 | 531.8 | 551.8 | 557.8 | 517.8 | 552.8 | 579.8 |
| 54 | 545.8 | 669.9 | 581.8 | 611.8 | 531.8 | 551.8 | 557.8 | 517.8 | 552.8 | 579.8 |
| 55 | 579.8 | 703.9 | 615.8 | 645.8 | 565.8 | 585.8 | 591.8 | 551.8 | 586.8 | 613.8 |
| 56 | 530.8 | 654.9 | 566.8 | 596.8 | 516.8 | 536.8 | 542.8 | 502.8 | 537.8 | 564.8 |

FIGURE 5B

|    | K     | L     | M     | N     | O     | P     | Q     | R     | S     | T     |
|----|-------|-------|-------|-------|-------|-------|-------|-------|-------|-------|
| 1  | 469.8 | 491.8 | 505.8 | 521.8 | 509.8 | 535.8 | 507.8 | 511.9 | 497.8 | 677.9 |
| 2  | 523.8 | 545.8 | 559.8 | 575.8 | 563.8 | 589.8 | 561.8 | 565.9 | 551.8 | 731.9 |
| 3  | 520.8 | 542.8 | 556.8 | 572.8 | 560.8 | 586.8 | 558.8 | 562.9 | 548.9 | 728.9 |
| 4  | 520.8 | 542.8 | 556.8 | 572.8 | 560.8 | 586.8 | 558.8 | 562.9 | 548.9 | 728.9 |
| 5  | 537.9 | 559.9 | 573.9 | 589.9 | 577.9 | 603.9 | 575.9 | 579.9 | 565.9 | 745.9 |
| 6  | 519.9 | 541.8 | 555.9 | 571.9 | 559.8 | 585.8 | 557.8 | 561.9 | 547.9 | 727.9 |
| 7  | 485.8 | 507.8 | 521.8 | 537.8 | 525.8 | 551.8 | 523.8 | 527.9 | 513.9 | 693.9 |
| 8  | 485.8 | 507.8 | 521.8 | 537.8 | 525.8 | 551.8 | 523.8 | 527.9 | 513.9 | 693.9 |
| 9  | 554.3 | 576.3 | 590.3 | 606.3 | 594.3 | 620.3 | 592.3 | 596.4 | 582.3 | 762.4 |
| 10 | 483.8 | 505.8 | 519.8 | 535.8 | 523.8 | 549.8 | 521.8 | 525.9 | 511.9 | 691.9 |
| 11 | 525.9 | 547.9 | 561.9 | 577.9 | 565.9 | 591.9 | 563.9 | 568.0 | 553.9 | 734.0 |
| 12 | 525.9 | 547.9 | 561.9 | 577.9 | 565.9 | 591.9 | 563.9 | 568.0 | 553.9 | 734.0 |
| 13 | 511.9 | 533.9 | 547.9 | 563.9 | 551.9 | 577.9 | 549.9 | 553.9 | 539.9 | 719.9 |
| 14 | 539.9 | 561.9 | 575.9 | 591.9 | 579.9 | 605.9 | 577.9 | 582.0 | 568.0 | 748.0 |
| 15 | 497.8 | 519.8 | 533.8 | 549.8 | 537.8 | 563.8 | 535.8 | 539.9 | 525.9 | 705.9 |
| 16 | 579.9 | 601.9 | 615.9 | 631.9 | 619.9 | 645.9 | 617.9 | 622.0 | 607.9 | 788.0 |
| 17 | 579.9 | 601.9 | 615.9 | 631.9 | 619.9 | 645.9 | 617.9 | 622.0 | 607.9 | 788.0 |
| 18 | 499.9 | 521.9 | 535.9 | 551.9 | 539.8 | 565.8 | 537.9 | 541.9 | 527.9 | 707.9 |
| 19 | 537.8 | 559.8 | 573.8 | 589.8 | 577.8 | 603.8 | 575.8 | 579.9 | 565.9 | 745.9 |
| 20 | 537.8 | 559.8 | 573.8 | 589.8 | 577.8 | 603.8 | 575.8 | 579.9 | 565.9 | 745.9 |
| 21 | 537.8 | 559.8 | 573.8 | 589.8 | 577.8 | 603.8 | 575.8 | 579.9 | 565.9 | 745.9 |
| 22 | 499.9 | 521.8 | 535.9 | 551.9 | 539.8 | 565.8 | 537.8 | 541.9 | 527.9 | 707.9 |
| 23 | 471.8 | 493.8 | 507.8 | 523.8 | 511.8 | 537.8 | 509.8 | 513.9 | 499.8 | 679.9 |
| 24 | 549.9 | 571.9 | 585.9 | 601.9 | 589.9 | 615.9 | 587.9 | 591.9 | 577.9 | 757.9 |
| 25 | 549.9 | 571.9 | 585.9 | 601.9 | 589.9 | 615.9 | 587.9 | 591.9 | 577.9 | 757.9 |
| 26 | 563.9 | 585.9 | 599.9 | 615.9 | 603.9 | 629.9 | 601.9 | 606.0 | 591.9 | 772.0 |
| 27 | 533.9 | 555.9 | 569.9 | 585.9 | 573.9 | 599.9 | 571.9 | 575.9 | 561.9 | 741.9 |
| 28 | 533.9 | 555.9 | 569.9 | 585.9 | 573.9 | 599.9 | 571.9 | 575.9 | 561.9 | 741.9 |
| 29 | 525.9 | 547.9 | 561.9 | 577.9 | 565.9 | 591.9 | 563.9 | 568.0 | 553.9 | 734.0 |
| 30 | 525.9 | 547.9 | 561.9 | 577.9 | 565.9 | 591.9 | 563.9 | 568.0 | 553.9 | 734.0 |
| 31 | 499.8 | 521.8 | 535.8 | 551.8 | 539.8 | 565.8 | 537.8 | 541.9 | 527.9 | 707.9 |
| 32 | 619.9 | 641.9 | 655.9 | 671.9 | 659.9 | 685.9 | 657.9 | 662.0 | 648.0 | 828.0 |

FIGURE 5C

| 33 | 541.9 | 563.9 | 577.9 | 593.9 | 581.9 | 607.9 | 579.9 | 584.0 | 570.0 | 750.0 |
|---|---|---|---|---|---|---|---|---|---|---|
| 34 | 533.9 | 555.9 | 569.9 | 585.9 | 573.9 | 599.9 | 571.9 | 575.9 | 561.9 | 741.9 |
| 35 | 497.9 | 519.8 | 533.9 | 549.8 | 537.8 | 563.8 | 535.8 | 539.9 | 525.9 | 705.9 |
| 36 | 563.9 | 585.8 | 599.9 | 615.9 | 603.8 | 629.8 | 601.8 | 605.9 | 591.9 | 771.9 |
| 37 | 483.8 | 505.8 | 519.8 | 535.8 | 523.8 | 549.8 | 521.8 | 525.9 | 511.9 | 691.9 |
| 38 | 545.9 | 567.9 | 581.9 | 597.9 | 585.9 | 611.9 | 583.9 | 587.9 | 573.9 | 754.0 |
| 39 | 564.0 | 586.0 | 600.0 | 616.0 | 604.0 | 630.0 | 602.0 | 606.1 | 592.0 | 772.1 |
| 40 | 578.0 | 600.0 | 614.0 | 630.0 | 618.0 | 644.0 | 616.0 | 620.1 | 606.0 | 786.1 |

| 41 | 549.9 | 571.9 | 585.9 | 601.9 | 589.9 | 615.9 | 587.9 | 591.9 | 577.9 | 757.9 |
|---|---|---|---|---|---|---|---|---|---|---|
| 42 | 602.9 | 624.9 | 638.9 | 654.9 | 642.9 | 668.9 | 640.9 | 645.0 | 631.0 | 811.0 |
| 43 | 565.9 | 587.9 | 601.9 | 617.9 | 605.9 | 631.9 | 603.9 | 607.9 | 593.9 | 773.9 |
| 44 | 501.8 | 523.8 | 537.8 | 553.8 | 541.8 | 567.8 | 539.8 | 543.8 | 529.8 | 709.9 |
| 45 | 529.9 | 551.9 | 565.9 | 581.9 | 569.9 | 595.9 | 567.9 | 571.9 | 557.9 | 738.0 |
| 46 | 515.9 | 537.8 | 551.9 | 567.9 | 555.8 | 581.8 | 553.8 | 557.9 | 543.9 | 723.9 |
| 47 | 515.9 | 537.8 | 551.9 | 567.9 | 555.8 | 581.8 | 553.8 | 557.9 | 543.9 | 723.9 |
| 48 | 473.8 | 495.8 | 509.8 | 525.8 | 513.8 | 539.8 | 511.8 | 515.8 | 501.8 | 681.8 |

| 49 | 486.8 | 508.8 | 522.8 | 538.8 | 526.8 | 552.8 | 524.8 | 528.9 | 514.8 | 694.9 |
|---|---|---|---|---|---|---|---|---|---|---|
| 50 | 472.8 | 494.8 | 508.8 | 524.8 | 512.8 | 538.8 | 510.8 | 514.9 | 500.8 | 680.9 |
| 51 | 498.8 | 520.8 | 534.8 | 550.8 | 538.8 | 564.8 | 536.8 | 540.9 | 526.8 | 706.9 |
| 52 | 501.7 | 523.7 | 537.7 | 553.7 | 541.7 | 567.7 | 539.7 | 543.8 | 529.7 | 709.8 |
| 53 | 543.8 | 565.8 | 579.8 | 595.8 | 583.8 | 609.8 | 581.8 | 585.9 | 571.8 | 751.9 |
| 54 | 543.8 | 565.8 | 579.8 | 595.8 | 583.8 | 609.8 | 581.8 | 585.9 | 571.8 | 751.9 |
| 55 | 577.8 | 599.8 | 613.8 | 629.8 | 617.8 | 643.8 | 615.8 | 619.9 | 605.8 | 785.9 |
| 56 | 528.8 | 550.8 | 564.8 | 580.8 | 568.8 | 594.8 | 566.8 | 570.9 | 556.8 | 736.9 |

FIGURE 5D

|    | A     | B     | C     | D     | E     | F     | G     | H     | I     | J     |
|----|-------|-------|-------|-------|-------|-------|-------|-------|-------|-------|
| 1  | 472.8 | 596.9 | 508.8 | 538.8 | 458.8 | 478.8 | 484.8 | 444.8 | 479.8 | 506.8 |
| 2  | 526.8 | 650.9 | 562.8 | 592.8 | 512.8 | 532.8 | 538.8 | 498.8 | 533.8 | 560.8 |
| 3  | 523.8 | 647.9 | 559.8 | 589.8 | 509.8 | 529.8 | 535.9 | 495.8 | 530.8 | 557.8 |
| 4  | 523.8 | 647.9 | 559.8 | 589.8 | 509.8 | 529.8 | 535.9 | 495.8 | 530.8 | 557.8 |
| 5  | 540.9 | 664.9 | 576.9 | 606.9 | 526.9 | 546.9 | 552.9 | 512.9 | 547.8 | 574.9 |
| 6  | 522.8 | 646.9 | 558.8 | 588.9 | 508.9 | 528.8 | 534.9 | 494.8 | 529.8 | 556.9 |
| 7  | 488.8 | 612.9 | 524.8 | 554.8 | 474.8 | 494.8 | 500.8 | 460.8 | 495.8 | 522.8 |
| 8  | 488.8 | 612.9 | 524.8 | 554.8 | 474.8 | 494.8 | 500.8 | 460.8 | 495.8 | 522.8 |
| 9  | 557.3 | 681.4 | 593.3 | 623.3 | 543.3 | 563.3 | 569.3 | 529.3 | 564.3 | 591.3 |
| 10 | 486.8 | 610.9 | 522.8 | 552.8 | 472.8 | 492.8 | 498.8 | 458.8 | 493.8 | 520.8 |
| 11 | 528.9 | 653.0 | 564.9 | 594.9 | 514.9 | 534.9 | 540.9 | 500.9 | 535.9 | 562.9 |
| 12 | 528.9 | 653.0 | 564.9 | 594.9 | 514.9 | 534.9 | 540.9 | 500.9 | 535.9 | 562.9 |
| 13 | 514.9 | 638.9 | 550.9 | 580.9 | 500.9 | 520.9 | 526.9 | 486.9 | 521.8 | 548.9 |
| 14 | 542.9 | 667.0 | 578.9 | 608.9 | 528.9 | 548.9 | 554.9 | 514.9 | 549.9 | 576.9 |
| 15 | 500.8 | 624.9 | 536.8 | 566.8 | 486.8 | 506.8 | 512.9 | 472.8 | 507.8 | 534.8 |
| 16 | 582.9 | 707.0 | 618.9 | 648.9 | 568.9 | 588.9 | 594.9 | 554.9 | 589.9 | 616.9 |
| 17 | 582.9 | 707.0 | 618.9 | 648.9 | 568.9 | 588.9 | 594.9 | 554.9 | 589.9 | 616.9 |
| 18 | 502.9 | 626.9 | 538.9 | 568.9 | 488.9 | 508.8 | 514.9 | 474.9 | 509.8 | 536.9 |
| 19 | 540.8 | 664.9 | 576.8 | 606.8 | 526.8 | 546.8 | 552.9 | 512.8 | 547.8 | 574.8 |
| 20 | 540.8 | 664.9 | 576.8 | 606.8 | 526.8 | 546.8 | 552.9 | 512.8 | 547.8 | 574.8 |
| 21 | 540.8 | 664.9 | 576.8 | 606.8 | 526.8 | 546.8 | 552.9 | 512.8 | 547.8 | 574.8 |
| 22 | 502.8 | 626.9 | 538.8 | 568.9 | 488.9 | 508.8 | 514.9 | 474.8 | 509.8 | 536.9 |
| 23 | 474.8 | 598.9 | 510.8 | 540.8 | 460.8 | 480.8 | 486.8 | 446.8 | 481.8 | 508.8 |
| 24 | 552.9 | 676.9 | 588.9 | 618.9 | 538.9 | 558.9 | 564.9 | 524.9 | 559.8 | 586.9 |
| 25 | 552.9 | 676.9 | 588.9 | 618.9 | 538.9 | 558.9 | 564.9 | 524.9 | 559.8 | 586.9 |
| 26 | 566.9 | 691.0 | 602.9 | 632.9 | 552.9 | 572.9 | 578.9 | 538.9 | 573.9 | 600.9 |
| 27 | 536.9 | 660.9 | 572.9 | 602.9 | 522.9 | 542.9 | 548.9 | 508.9 | 543.8 | 570.9 |
| 28 | 536.9 | 660.9 | 572.9 | 602.9 | 522.9 | 542.9 | 548.9 | 508.9 | 543.8 | 570.9 |
| 29 | 528.9 | 653.0 | 564.9 | 594.9 | 514.9 | 534.9 | 540.9 | 500.9 | 535.9 | 562.9 |
| 30 | 528.9 | 653.0 | 564.9 | 594.9 | 514.9 | 534.9 | 540.9 | 500.9 | 535.9 | 562.9 |
| 31 | 502.8 | 626.9 | 538.8 | 568.8 | 488.8 | 508.8 | 514.8 | 474.8 | 509.8 | 536.8 |
| 32 | 622.9 | 747.0 | 658.9 | 688.9 | 608.9 | 628.9 | 634.9 | 594.9 | 629.9 | 656.9 |

FIGURE 6A

| | | | | | | | | | |
|---|---|---|---|---|---|---|---|---|---|
| 33 | 544.9 | 669.0 | 580.9 | 610.9 | 530.9 | 550.9 | 557.0 | 516.9 | 551.9 | 578.9 |
| 34 | 536.9 | 660.9 | 572.9 | 602.9 | 522.9 | 542.9 | 548.9 | 508.9 | 543.8 | 570.9 |
| 35 | 500.8 | 624.9 | 536.8 | 566.8 | 486.9 | 506.8 | 512.9 | 472.8 | 507.8 | 534.9 |
| 36 | 566.8 | 690.9 | 602.8 | 632.9 | 552.9 | 572.8 | 578.9 | 538.8 | 573.8 | 600.9 |
| 37 | 486.8 | 610.9 | 522.8 | 552.8 | 472.8 | 492.8 | 498.8 | 458.8 | 493.8 | 520.8 |
| 38 | 548.9 | 672.9 | 584.9 | 614.9 | 534.9 | 554.9 | 560.9 | 520.9 | 555.8 | 582.9 |
| 39 | 567.0 | 691.1 | 603.0 | 633.0 | 553.0 | 573.0 | 579.0 | 539.0 | 574.0 | 601.0 |
| 40 | 581.0 | 705.1 | 617.0 | 647.0 | 567.0 | 587.0 | 593.0 | 553.0 | 588.0 | 615.0 |
| 41 | 552.9 | 676.9 | 588.9 | 618.9 | 538.9 | 558.9 | 564.9 | 524.9 | 559.8 | 586.9 |
| 42 | 605.9 | 730.0 | 641.9 | 671.9 | 591.9 | 611.9 | 618.0 | 577.9 | 612.9 | 639.9 |
| 43 | 568.9 | 692.9 | 604.9 | 634.9 | 554.9 | 574.9 | 580.9 | 540.9 | 575.8 | 602.9 |
| 44 | 504.8 | 628.8 | 540.8 | 570.8 | 490.8 | 510.8 | 516.8 | 476.8 | 511.7 | 538.8 |
| 45 | 532.9 | 656.9 | 568.9 | 598.9 | 518.9 | 538.9 | 544.9 | 504.9 | 539.8 | 566.9 |
| 46 | 518.8 | 642.9 | 554.8 | 584.9 | 504.9 | 524.8 | 530.9 | 490.8 | 525.8 | 552.9 |
| 47 | 518.8 | 642.9 | 554.8 | 584.9 | 504.9 | 524.8 | 530.9 | 490.8 | 525.8 | 552.9 |
| 48 | 476.8 | 600.8 | 512.8 | 542.8 | 462.8 | 482.8 | 488.8 | 448.8 | 483.7 | 510.8 |
| 49 | 489.8 | 613.9 | 525.8 | 555.8 | 475.8 | 495.8 | 501.8 | 461.8 | 496.8 | 523.8 |
| 50 | 475.8 | 599.9 | 511.8 | 541.8 | 461.8 | 481.8 | 487.8 | 447.8 | 482.8 | 509.8 |
| 51 | 501.8 | 625.9 | 537.8 | 567.8 | 487.8 | 507.8 | 513.8 | 473.8 | 508.8 | 535.8 |
| 52 | 504.7 | 628.8 | 540.7 | 570.7 | 490.7 | 510.7 | 516.7 | 476.7 | 511.7 | 538.7 |
| 53 | 546.8 | 670.9 | 582.8 | 612.8 | 532.8 | 552.8 | 558.8 | 518.8 | 553.8 | 580.8 |
| 54 | 546.8 | 670.9 | 582.8 | 612.8 | 532.8 | 552.8 | 558.8 | 518.8 | 553.8 | 580.8 |
| 55 | 580.8 | 704.9 | 616.8 | 646.8 | 566.8 | 586.8 | 592.8 | 552.8 | 587.8 | 614.8 |
| 56 | 531.8 | 655.9 | 567.8 | 597.8 | 517.8 | 537.8 | 543.8 | 503.8 | 538.8 | 565.8 |

FIGURE 6B

|    | K     | L     | M     | N     | O     | P     | Q     | R     | S     | T     |
|----|-------|-------|-------|-------|-------|-------|-------|-------|-------|-------|
| 1  | 470.8 | 492.8 | 506.8 | 522.8 | 510.8 | 536.8 | 508.8 | 512.9 | 498.8 | 678.9 |
| 2  | 524.8 | 546.8 | 560.8 | 576.8 | 564.8 | 590.8 | 562.8 | 566.9 | 552.8 | 732.9 |
| 3  | 521.8 | 543.8 | 557.8 | 573.8 | 561.8 | 587.8 | 559.8 | 563.9 | 549.9 | 729.9 |
| 4  | 521.8 | 543.8 | 557.8 | 573.8 | 561.8 | 587.8 | 559.8 | 563.9 | 549.9 | 729.9 |
| 5  | 538.9 | 560.9 | 574.9 | 590.9 | 578.9 | 604.9 | 576.9 | 580.9 | 566.9 | 746.9 |
| 6  | 520.9 | 542.8 | 556.9 | 572.9 | 560.8 | 586.8 | 558.8 | 562.9 | 548.9 | 728.9 |
| 7  | 486.8 | 508.8 | 522.8 | 538.8 | 526.8 | 552.8 | 524.8 | 528.9 | 514.9 | 694.9 |
| 8  | 486.8 | 508.8 | 522.8 | 538.8 | 526.8 | 552.8 | 524.8 | 528.9 | 514.9 | 694.9 |
| 9  | 555.3 | 577.3 | 591.3 | 607.3 | 595.3 | 621.3 | 593.3 | 597.4 | 583.3 | 763.4 |
| 10 | 484.8 | 506.8 | 520.8 | 536.8 | 524.8 | 550.8 | 522.8 | 526.9 | 512.9 | 692.9 |
| 11 | 526.9 | 548.9 | 562.9 | 578.9 | 566.9 | 592.9 | 564.9 | 569.0 | 554.9 | 735.0 |
| 12 | 526.9 | 548.9 | 562.9 | 578.9 | 566.9 | 592.9 | 564.9 | 569.0 | 554.9 | 735.0 |
| 13 | 512.9 | 534.9 | 548.9 | 564.9 | 552.9 | 578.9 | 550.9 | 554.9 | 540.9 | 720.9 |
| 14 | 540.9 | 562.9 | 576.9 | 592.9 | 580.9 | 606.9 | 578.9 | 583.0 | 569.0 | 749.0 |
| 15 | 498.8 | 520.8 | 534.8 | 550.8 | 538.8 | 564.8 | 536.8 | 540.9 | 526.9 | 706.9 |
| 16 | 580.9 | 602.9 | 616.9 | 632.9 | 620.9 | 646.9 | 618.9 | 623.0 | 608.9 | 789.0 |
| 17 | 580.9 | 602.9 | 616.9 | 632.9 | 620.9 | 646.9 | 618.9 | 623.0 | 608.9 | 789.0 |
| 18 | 500.9 | 522.9 | 536.9 | 552.9 | 540.8 | 566.8 | 538.9 | 542.9 | 528.9 | 708.9 |
| 19 | 538.8 | 560.8 | 574.8 | 590.8 | 578.8 | 604.8 | 576.8 | 580.9 | 566.9 | 746.9 |
| 20 | 538.8 | 560.8 | 574.8 | 590.8 | 578.8 | 604.8 | 576.8 | 580.9 | 566.9 | 746.9 |
| 21 | 538.8 | 560.8 | 574.8 | 590.8 | 578.8 | 604.8 | 576.8 | 580.9 | 566.9 | 746.9 |
| 22 | 500.9 | 522.8 | 536.9 | 552.9 | 540.8 | 566.8 | 538.8 | 542.9 | 528.9 | 708.9 |
| 23 | 472.8 | 494.8 | 508.8 | 524.8 | 512.8 | 538.8 | 510.8 | 514.9 | 500.8 | 680.9 |
| 24 | 550.9 | 572.9 | 586.9 | 602.9 | 590.9 | 616.9 | 588.9 | 592.9 | 578.9 | 758.9 |
| 25 | 550.9 | 572.9 | 586.9 | 602.9 | 590.9 | 616.9 | 588.9 | 592.9 | 578.9 | 758.9 |
| 26 | 564.9 | 586.9 | 600.9 | 616.9 | 604.9 | 630.9 | 602.9 | 607.0 | 592.9 | 773.0 |
| 27 | 534.9 | 556.9 | 570.9 | 586.9 | 574.9 | 600.9 | 572.9 | 576.9 | 562.9 | 742.9 |
| 28 | 534.9 | 556.9 | 570.9 | 586.9 | 574.9 | 600.9 | 572.9 | 576.9 | 562.9 | 742.9 |
| 29 | 526.9 | 548.9 | 562.9 | 578.9 | 566.9 | 592.9 | 564.9 | 569.0 | 554.9 | 735.0 |
| 30 | 526.9 | 548.9 | 562.9 | 578.9 | 566.9 | 592.9 | 564.9 | 569.0 | 554.9 | 735.0 |
| 31 | 500.8 | 522.8 | 536.8 | 552.8 | 540.8 | 566.8 | 538.8 | 542.9 | 528.9 | 708.9 |
| 32 | 620.9 | 642.9 | 656.9 | 672.9 | 660.9 | 686.9 | 658.9 | 663.0 | 649.0 | 829.0 |
| 33 | 542.9 | 564.9 | 578.9 | 594.9 | 582.9 | 608.9 | 580.9 | 585.0 | 571.0 | 751.0 |
| 34 | 534.9 | 556.9 | 570.9 | 586.9 | 574.9 | 600.9 | 572.9 | 576.9 | 562.9 | 742.9 |
| 35 | 498.9 | 520.8 | 534.9 | 550.8 | 538.8 | 564.8 | 536.8 | 540.9 | 526.9 | 706.9 |
| 36 | 564.9 | 586.8 | 600.9 | 616.9 | 604.8 | 630.8 | 602.8 | 606.9 | 592.9 | 772.9 |
| 37 | 484.8 | 506.8 | 520.8 | 536.8 | 524.8 | 550.8 | 522.8 | 526.9 | 512.9 | 692.9 |
| 38 | 546.9 | 568.9 | 582.9 | 598.9 | 586.9 | 612.9 | 584.9 | 588.9 | 574.9 | 755.0 |
| 39 | 565.0 | 587.0 | 601.0 | 617.0 | 605.0 | 631.0 | 603.0 | 607.1 | 593.0 | 773.1 |
| 40 | 579.0 | 601.0 | 615.0 | 631.0 | 619.0 | 645.0 | 617.0 | 621.1 | 607.0 | 787.1 |

FIGURE 6C

| 41 | 550.9 | 572.9 | 586.9 | 602.9 | 590.9 | 616.9 | 588.9 | 592.9 | 578.9 | 758.9 |
|---|---|---|---|---|---|---|---|---|---|---|
| 42 | 603.9 | 625.9 | 639.9 | 655.9 | 643.9 | 669.9 | 641.9 | 646.0 | 632.0 | 812.0 |
| 43 | 566.9 | 588.9 | 602.9 | 618.9 | 606.9 | 632.9 | 604.9 | 608.9 | 594.9 | 774.9 |
| 44 | 502.8 | 524.8 | 538.8 | 554.8 | 542.8 | 568.8 | 540.8 | 544.8 | 530.8 | 710.9 |
| 45 | 530.9 | 552.9 | 566.9 | 582.9 | 570.9 | 596.9 | 568.9 | 572.9 | 558.9 | 739.0 |
| 46 | 516.9 | 538.8 | 552.9 | 568.9 | 556.8 | 582.8 | 554.8 | 558.9 | 544.9 | 724.9 |
| 47 | 516.9 | 538.8 | 552.9 | 568.9 | 556.8 | 582.8 | 554.8 | 558.9 | 544.9 | 724.9 |
| 48 | 474.8 | 496.8 | 510.8 | 526.8 | 514.8 | 540.8 | 512.8 | 516.8 | 502.8 | 682.8 |

| 49 | 487.8 | 509.8 | 523.8 | 539.8 | 527.8 | 553.8 | 525.8 | 529.9 | 515.8 | 695.9 |
|---|---|---|---|---|---|---|---|---|---|---|
| 50 | 473.8 | 495.8 | 509.8 | 525.8 | 513.8 | 539.8 | 511.8 | 515.9 | 501.8 | 681.9 |
| 51 | 499.8 | 521.8 | 535.8 | 551.8 | 539.8 | 565.8 | 537.8 | 541.9 | 527.8 | 707.9 |
| 52 | 502.7 | 524.7 | 538.7 | 554.7 | 542.7 | 568.7 | 540.7 | 544.8 | 530.7 | 710.8 |
| 53 | 544.8 | 566.8 | 580.8 | 596.8 | 584.8 | 610.8 | 582.8 | 586.9 | 572.8 | 752.9 |
| 54 | 544.8 | 566.8 | 580.8 | 596.8 | 584.8 | 610.8 | 582.8 | 586.9 | 572.8 | 752.9 |
| 55 | 578.8 | 600.8 | 614.8 | 630.8 | 618.8 | 644.8 | 616.8 | 620.9 | 606.8 | 786.9 |
| 56 | 529.8 | 551.8 | 565.8 | 581.8 | 569.8 | 595.8 | 567.8 | 571.9 | 557.8 | 737.9 |

FIGURE 6D

TREATMENT FOR DIABETES AND OBESITY AS WELL AS METHOD OF SCREENING COMPOUNDS USEFUL FOR SUCH TREATMENTS

This application claims the benefit of U.S. Provisional Patent Application Ser. No. 60/693,192, filed Jun. 23, 2005, which is hereby incorporated by reference in its entirety.

FIELD OF THE INVENTION

The present invention is directed to a treatment for diabetes and obesity as well as a method for screening compounds which could be useful for treating these diseases.

BACKGROUND OF THE INVENTION

Forward chemical genetics is an emerging field that offers powerful tools to search for novel drug candidates and their targets (Lokey, R. S., "Forward Chemical Genetics: Progress and Obstacles on the Path to a New Pharmacopoeia," *Curr Opin Chem Biol* 7:91-6 (2003); Tan, D. S., "Sweet Surrender to Chemical Genetics," *Nature Biotech.* 20:561-563 (2002); Specht et al., "The Emerging Power of Chemical Genetics," *Current Opinion in Cell Biology* 14:155-159 (2002); and Schreiber, S. L., "The Small Molecule Approach to Biology," *Chem Eng News*, pp. 51-61 (2003)). It differs from classical genetics by substituting small molecules for mutation inducing agents or X-ray irradiation. Using combinatorial techniques, (Jung, G., "Combinatorial Chemistry: Synthesis, Analysis, Screening," Wiley-VCH, Weinheim: Cambridge (1999); Nicolaou et al., "Handbook of Combinatorial Chemistry: Drugs, Catalysts, Materials," Wiley-VCH, Weinheim (2002)) one is able to rapidly screen a large number of small molecules and identify those that induce a novel phenotype in a cellular or embryonic system. Once a phenotypic effect is found, the next step is to identify the biological target using an affinity matrix made of the immobilized hit compound. However, the synthesis of an efficient affinity matrix without loss of activity by the hit compound has been shown to be challenging, or sometimes totally impossible due to the difficulties of adequate linker attachment.

Insulin or insulin-like growth factors (IGF) play essential roles in growth, development, and the maintenance of normal metabolic homeostasis including glucose uptake from the blood stream (Le Roith et al., "Recent Advances in Our Understanding of Insulin Action and Insulin Resistance," *Diabetes Care* 24:588-597 (2001)). These signaling pathways are closely related to diabetic disease/obesity/aging processes and are highly conserved from yeast to humans, but the biochemical mechanism is not yet fully understood. A small molecule regulator for insulin/IGF downstream of the target protein will provide a useful tool and information to dissect the signaling mechanism.

In *C. elegans*, the Daf-2 (36% identical to the insulin receptor and 35% identical to the IGF-1 of human; there is no known insulin receptor in *C. elegans* (Le Roith et al., "Recent Advances in Our Understanding of Insulin Action and Insulin Resistance," *Diabetes Care* 24:588-597 (2001)) signaling pathway controls food intake, metabolism, growth and life span, and shares, at least partially, common down-stream players with mammalian cells, including phosphoinositide-3 kinase (PI3K). PI3K catalyzes the conversion of phosphatidyl inositol[4,5]bisphosphate ($PIP_2$) into the active signaling molecule, phosphatidyl inositol[3,4,5]trisphosphate ($PIP_3$), and one of the important end results in mammalian cells, is glucose uptake into the cell via protein kinase B (Akt) activation (Hawkins et al., "Platelet-Derived Growth-Factor Stimulates Synthesis of Ptdlns(3,4,5)P3 by Activating a Ptdlns(4,5)P2 3-Oh Kinase," *Nature* 358:157-159 (1992)). A single mutation of a kinase domain of Daf-2 (i.e., e1370), which causes constitutive arrest at the dauer larval stage (at the restrictive temperature 25° C., whereas normal phenotype occurs at the permissive temperature of 16° C.), was chosen for this study (Gems et al., "Two Pleiotropic Classes of Daf-2 Mutation Affect Larval Arrest, Adult Behavior, Reproduction and Longevity in *Caenorhabditis elegans*," *Genetics* 150:129-155 (1998)). Dauer larvae have slowed metabolic rates, store large amounts of fat, and live longer than reproductive adults. The uniquely small size phenotype compared to a normal adult worm serves as a simple readout for the primary screening (Carroll et al., "Model Systems in Drug Discovery: Chemical Genetics Meets Genomics," *Pharmacol Ther* 99:183-220 (2003); Choy et al., "Fluoxetine-Resistant Mutants in *C. elegans* Define a Novel Family of Transmembrane Proteins," *Mol Cell* 4:143-52 (1999)).

The present invention overcomes the problem of inefficient affinity matrix synthesis and allows for the isolation of hydrophobically-capped bioactive compounds for use in treating patients with diabetes and obesity.

SUMMARY OF THE INVENTION

The present invention relates to a compound according to the formula:

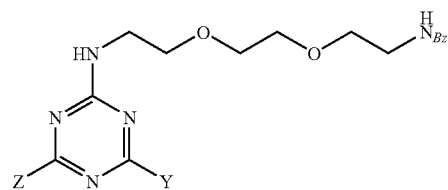

where Z is an amine, phenoxy, or thiol-containing group and Y is an alkyl-containing amine.

Another aspect of the present invention relates to a process of synthesizing a compound having the formula:

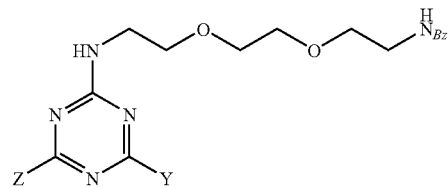

where Z is an amine, phenoxy, or thiol-containing group and Y is an alkyl-containing amine. The process includes providing an immobilized precursor compound having the formula:

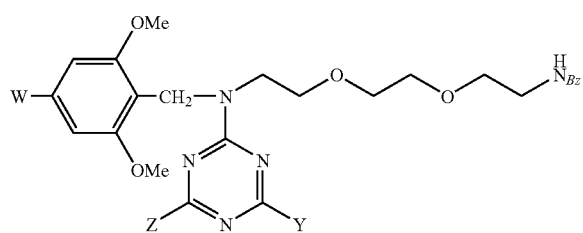

where W is a solid support. The immobilized precursor compound is then converted to the product compound.

Another aspect of the present invention relates to a method of treating a subject for diabetes and obesity. The method includes treating a subject with a compound having the formula:

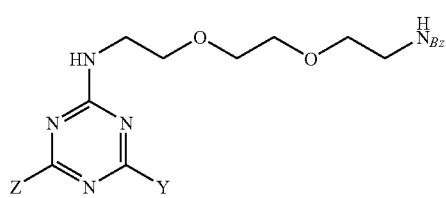

where Z is an amine, phenoxy, or thiol-containing group and Y is an alkyl-containing amine, under conditions effective to treat diabetes and obesity.

Another aspect of the present invention relates to a method of treating a subject for diabetes and obesity by treating the subject with a compound which inhibits GAPDH, under conditions effective to treat diabetes and obesity.

Another aspect of the present invention relates to a method of screening compounds for their effectiveness in modulating diabetes and obesity. The screening of the compounds is accomplished by providing both a candidate compound and GAPDH. The candidate compound and GAPDH are then contacted under conditions effective for the candidate compound to bind to the GAPDH, thereby determining the compound's potential effectiveness to modulate diabetes and obesity.

Another aspect of the present invention relates to a method of screening for compounds effective in modulating diabetes and obesity. This is accomplished by providing both a candidate compound and a *C. elegans* strain capable of transforming into a dauer state. The candidate compound and the *C. elegans* strain are then contacted. The compound which inhibits dauer formation is effective in modulating diabetes and obesity.

The hydrophobic group capped linker library approach of the present invention accelerates the conversion of a hit compound to an efficient affinity matrix, thus making forward chemical genetics a more systematic strategy. This library also makes use of a hydrophobic tag that renders the library molecules highly cell membrane permeable.

The hydrophobic tag method not only provides for a straightforward method of isolation of the target protein without compromising the lead compound's activity or performing further SAR experiments but also allows for small molecules to readily penetrate across the cell membrane.

The present invention provides a unique technique to introduce hydrophobic caps to linker triazine libraries, enhancing the tissue permeability of the compounds. Insulin signaling pathway is a evolutionary conserved mechanism. In organisms ranging from yeast to mice, mutations in insulin or insulin-like receptors extend life span but also cause glycogen or fat accumulation and dwarfism. In this mutant of *C. elegans*, several compounds which overcame the mutation of the insulin receptor were screened and the target of those compounds were identified as GAPDH. Blocking translation of GAPDH by RNAi overcame this mutation also. These compounds are novel GAPDH inhibitors with potentially insulin mimetic activity. As a result, they can be used to treat patients with diabetes and obesity.

BRIEF DESCRIPTION OF THE DRAWINGS

FIGS. 5A-D show a table depicting the exact molecular weights of TGBz library compounds.

FIGS. 6A-D show a table depicting the LC-MS measured masses of TGBz library compounds.

DETAILED DESCRIPTION OF THE INVENTION

The present invention relates to a compound having the formula:

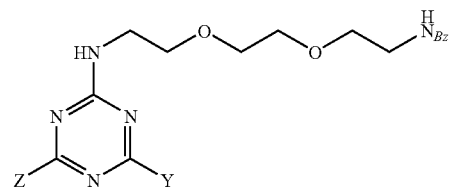

where Z is an amine, phenoxy, or thiol-containing group and Y is an alkyl-containing amine.

The Z group may have the structure of one of Formulae 1 to 20, as follows in Table 1:

TABLE 1

1

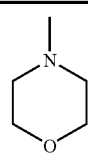

TABLE 1-continued
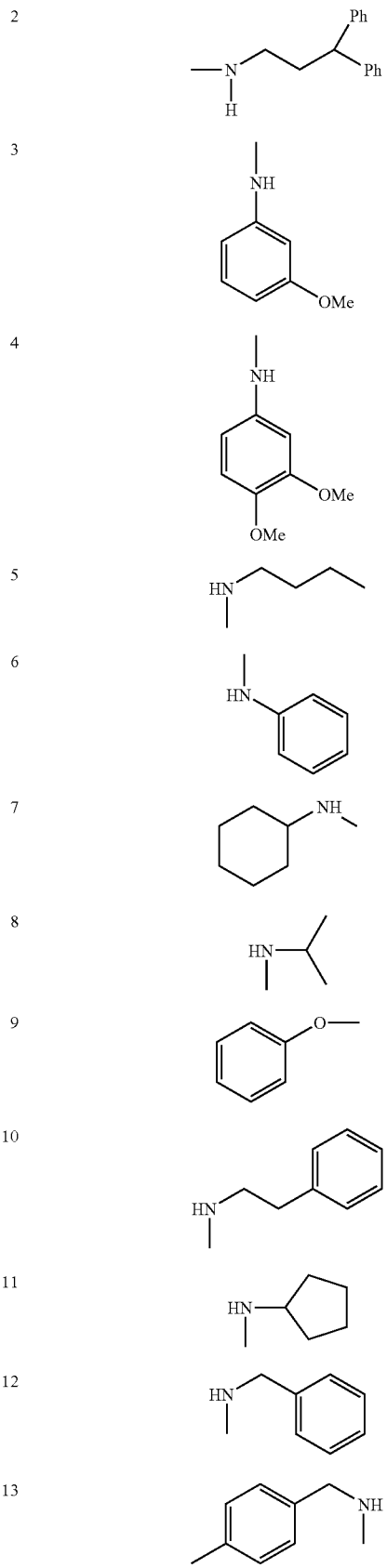
TABLE 1-continued
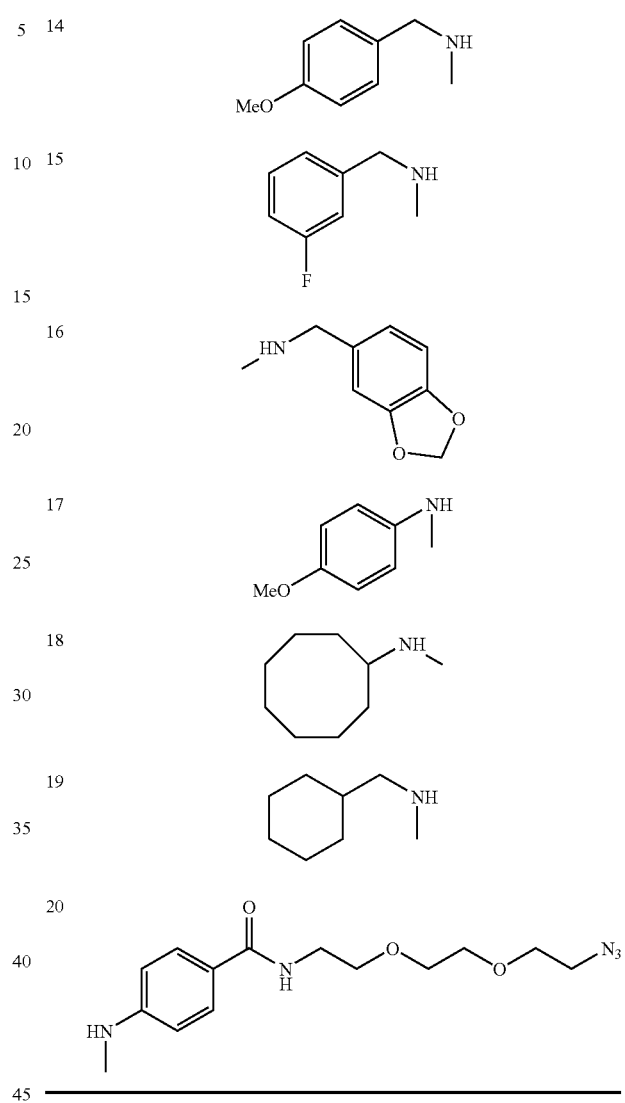
The Y group may have the structure of one of Formulae 1 to 56, as follows in Table 2:
TABLE 2
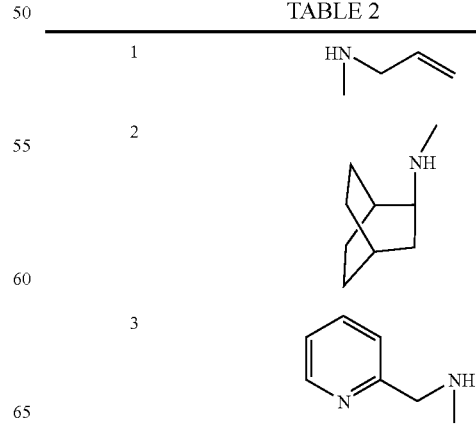

TABLE 2-continued
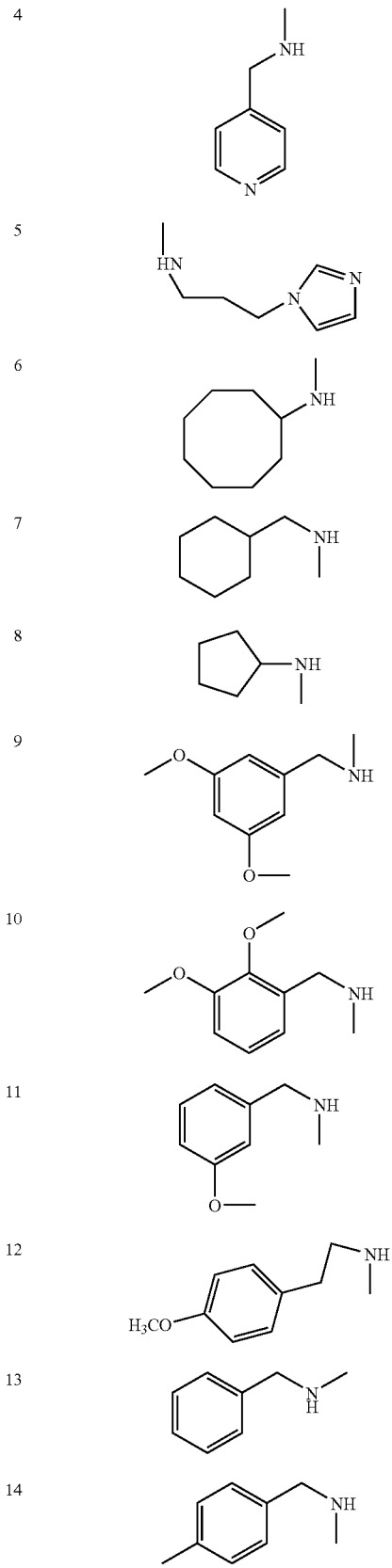
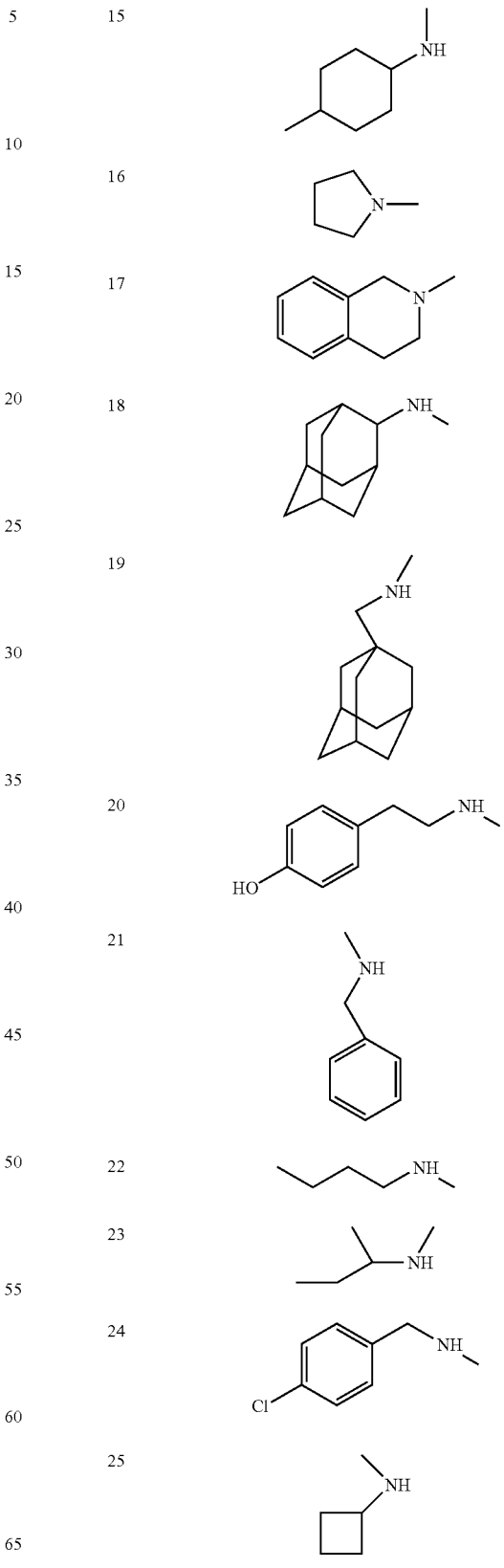

TABLE 2-continued
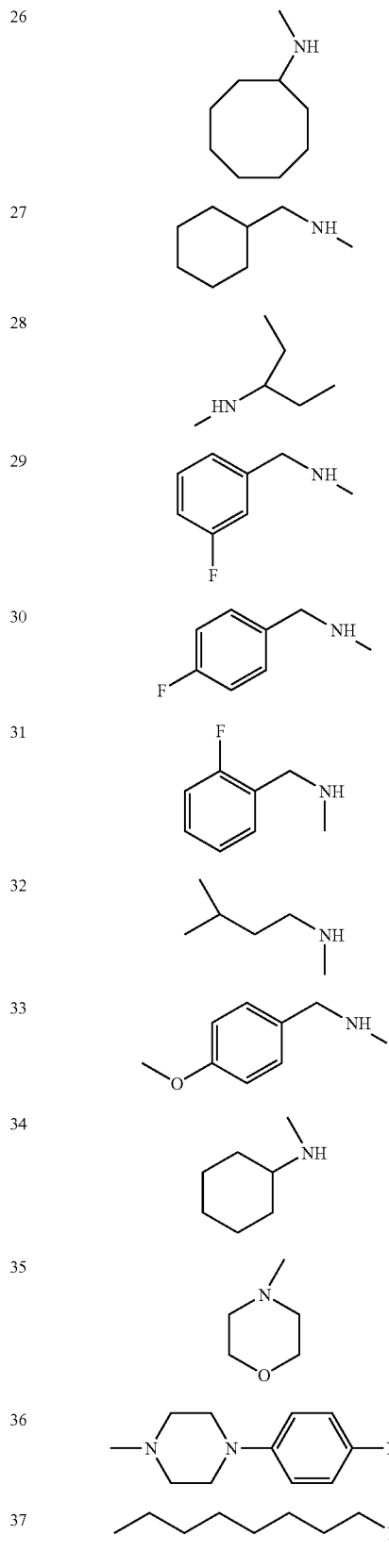
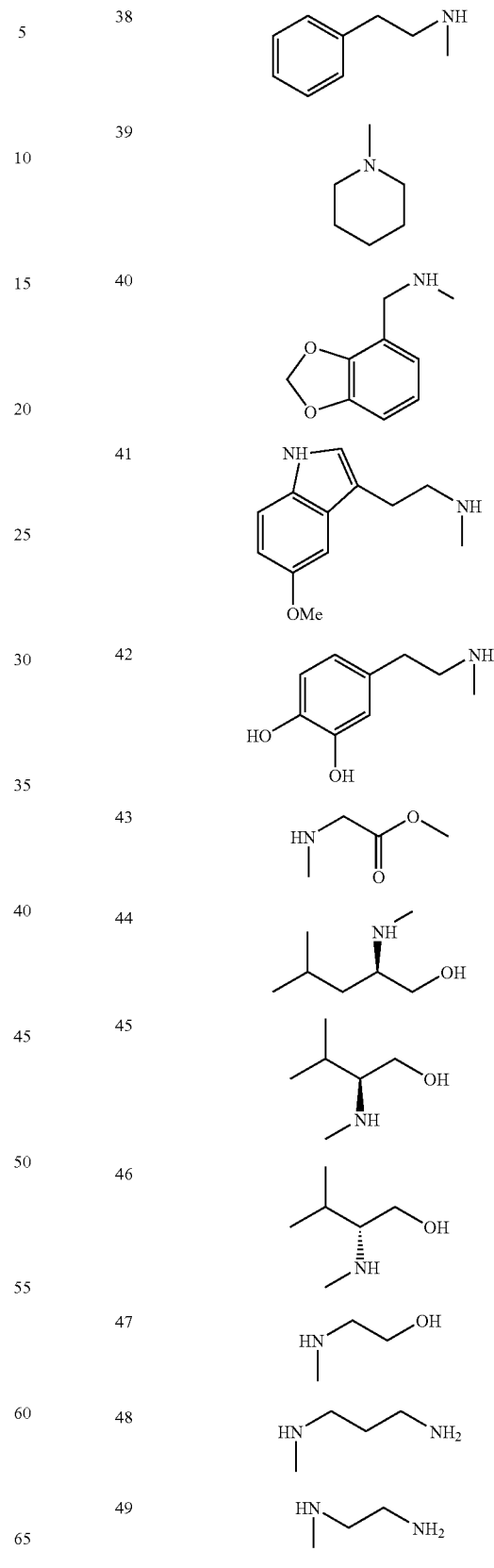

TABLE 2-continued

| 50 | 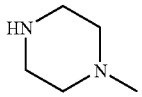 |
| 51 | 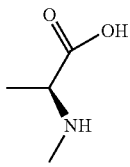 |
| 52 | 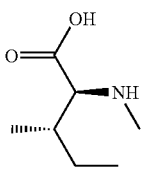 |
| 53 | 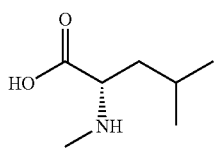 |
| 54 | 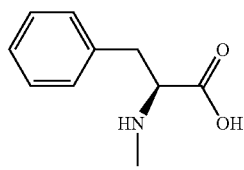 |
| 55 | 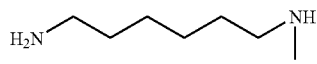 |
| 56 | 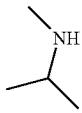 |

A preferred embodiment of the compound of the present invention has the formula:

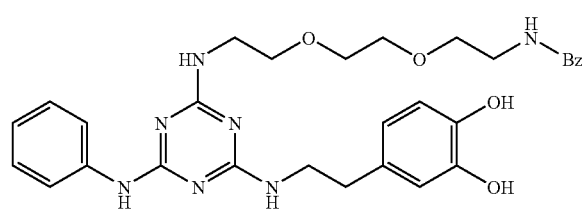

Figure 1:
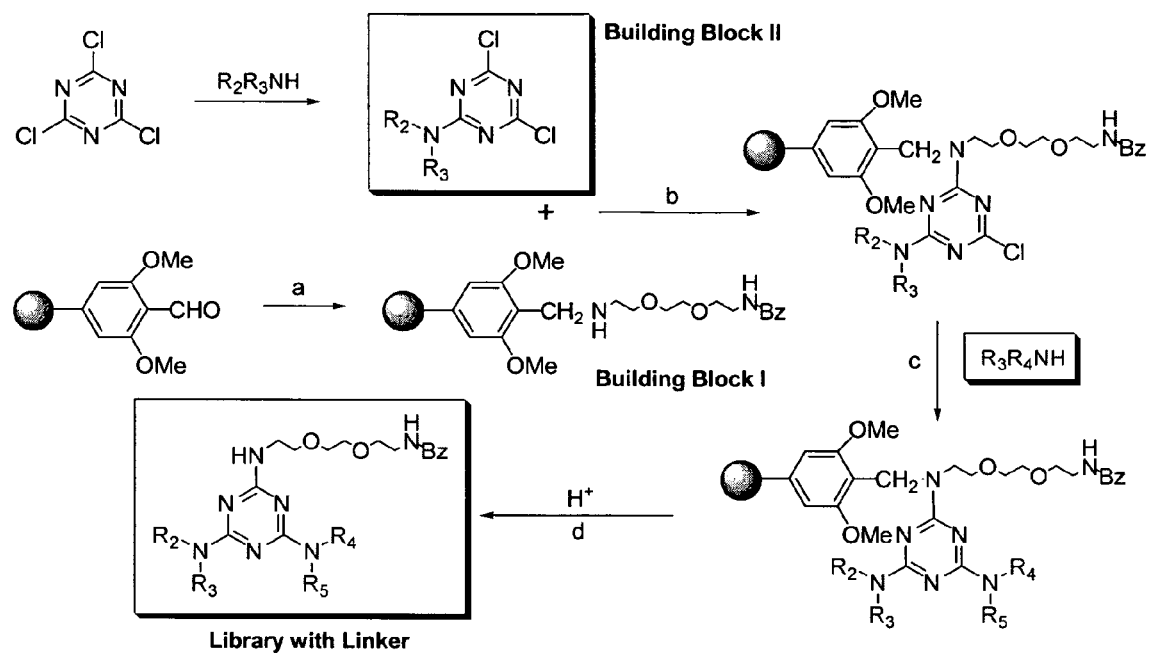
FIG. 1 shows the synthesis scheme of the TGBz linker library in accordance with the present invention.

Another aspect of the present invention relates to a process for synthesizing a product compound with the formula:

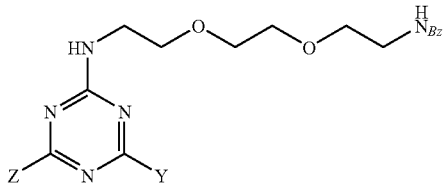

where Z is an amine, phenoxy, or thiol-containing group and Y is an alkyl-containing amine. This process is illustrated in FIG. 1. The process includes providing an immobilized precursor compound with the formula:

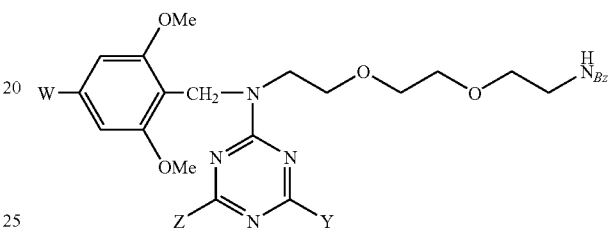

where W is a solid support.

The immobilized precursor compound is converted to the product compound. In particular, the immobilized precursor compound is cleaved using 10% trifluoroacetic acid (TFA) in dichloromethane for 30 min at room temperature and washed with dichloromethane. Free hydroxyl containing compounds were further treated with a piperazine resin in 0.5 ml THF at room temperature for 5 hrs to cleave the trifluoroacetic ester that was formed upon treatment with TFA. The resin was filtered out and washed with THF. The purity and identity of all the products were monitored by LC-MS at 250 nm.

The immobilized precursor is synthesized by providing a first intermediate compound with the formula:

Y—H and an immobilized intermediate compound with the formula:

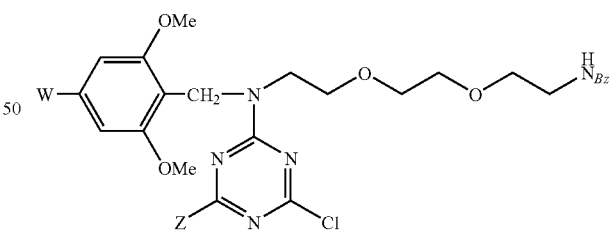

The immobilized precursor and the immobilized intermediate compound are reacted under conditions effective to form the immobilized precursor compound. In particular, desired amines (4 equiv.) were added to the resin (10 mg), coupled with Building Block I and Building Block II, in DIEA (8 µL) and 1 mL of NMP: n-BuOH (1:1). The reaction mixture was heated to 120° C. for 3 hr. The resin was washed with N,N-dimethylformamide (DMF) (5 times) alternatively with dichloromethane and methanol (5 times) and finally with dichloromethane (5 times). The resin was dried under vacuum.

The immobilized intermediate compound may be produced by reacting a secondary intermediate compound having the formula:

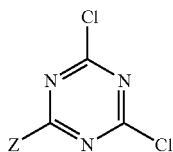

with a secondary immobilized intermediate compound having the formula:

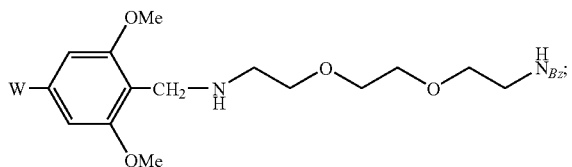

The compounds are allowed to react under conditions effective to produce the immobilized intermediate compound. In particular, the secondary intermediate compound is added to the secondary immobilized intermediate compound in DIEA and anhydrous THF at room temperature. The reaction mixture was heated to 60° C. for 3 hrs. and filtered. The resin was washed with DMF (5 times) alternatively with dichloromethane and methanol (5 times) and finally dichloromethane (5 times). The resin was dried under vacuum.

The second intermediate compound may be produced by reacting a first starting compound with the formula:

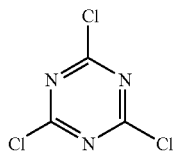

with a second starting compound with the formula:

under conditions effective to produce the secondary intermediate compound. In particular, cyanuric trichloride (1 equiv.) was dissolved in THF with DIEA (10 equiv.) at 0° C. The desired amine/aniline (1.2 equiv.) in THF was added dropwise. For addition of phenoxy to cyanuric chloride, the same reaction conditions were followed except 2.5 equiv. of $K_2CO_3$ was used instead of DIEA. The reaction mixture was stirred and monitored by TLC. Reaction time was 45 min. to 1 hr. A solid precipitate slowly formed. Upon completion of the reaction, the reaction mixture was quickly filtered though a plug of flash silica and washed with EA. The filtrate was evaporated in vacuo. The resulting products were purified using flash column chromatography (particle size 32-63 μm).

The second immobilized compound may be produced by converting an immobilized reactant compound with the formula:

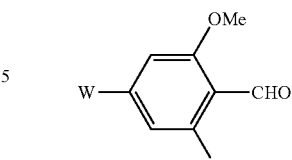

under conditions effective to produce the secondary immobilized compound. In particular, a TGBz linker (2.8 mmole, 5 equiv.) is added to a suspension of the PAL aldehyde resin (1.3 g, 1.43 mmole) in anhydrous tetrahydrofuran (THF) (50 mL containing 2% of acetic acid) at room temperature. The reaction mixture was shaken for 1 hr. at room temperature followed by addition of sodium triacetoxyborohydride (2.1 g, 9.9 mmole, 7 equiv.). The reaction mixture was stirred for 12 hrs. and filtered. The resin was washed with N,N-dimethylformamide (DMF) (5 times) alternatively with dichloromethane and methanol (MeOH) (5 times) and finally with dichloromethane (5 times). The resin was dried under vacuum.

Suitable solid supports W for carrying out the process for synthesizing the product compound include particles, strands, precipitates, gels, sheets, tubing, spheres, containers, capillaries, pads, slices, films, plates, slides, discs, membranes, etc. These solid supports can be made from a wide variety of materials, including polymers, plastics, ceramics, polysaccharides, silica or silica-based materials, carbon, metals, inorganic glasses, membranes, or composites thereof. The substrate is preferably flat but may take on a variety of alternative surface configurations. For example, the substrate may contain raised or depressed regions on which the synthesis takes place. The substrate and its surface preferably form a rigid support on which to carry out the reactions described herein. Other substrate materials will be readily apparent to those of ordinary skill in the art upon review of this disclosure.

The surface of the substrate can be etched using well known techniques to provide for desired surface features. For example, by way of the formation of trenches, v-grooves, mesa structures, raised platforms, or the like, the synthesis regions may be more closely placed within the focus point of impinging light, be provided with reflective "mirror" structures for maximization of light collection from fluorescent sources, or the like.

To attach the precursor compound to support W, the surface can be functionalized. Preferably, the surface functionalities will be reactive groups such as silanol, olefin, amino, hydroxyl, aldehyde, keto, halo, acyl halide, or carboxyl groups. In some cases, such functionalities preexist on the substrate. For example, silica-based materials have silanol groups, polysaccharides have hydroxyl groups, and synthetic polymers can contain a broad range of functional groups, depending on which monomers they are produced from. Alternatively, if the substrate does not contain the desired functional groups, such groups can be coupled onto the substrate in one or more steps. Hydroxyl groups become incorporated into stable carbamate (urethane) linkages by several methods. Amino functions can be acylated directly, whereas carboxyl groups are activated, e.g., with N,N'-carbonyldiimidazole or water-soluble carbodiimides, and reacted with an amino-functionalized compound.

Preferably, the precursor compound is attached to the support by a chemical linker. The linker molecules are preferably of sufficient length to permit polymers in a completed substrate to interact freely with molecules exposed to the substrate. The linker molecules should be 6-50 atoms long to provide sufficient exposure. The linker molecules may be, for example, aryl acetylene, ethylene glycol oligomers containing 2-10 monomer units, diamines, diacids, amino acids, or combinations thereof.

The design of the tagged library was based on a triazine scaffold due to its ease of manipulation and structural similarity to purine and pyrimidine, which have already been demonstrated to be active in various biological systems (Chang et al., "Purine-Based Inhibitors of Inositol-1,4,5-Trisphosphate-3-Kinase," *Chembiochem* 3:897-901 (2002); Verdugo et al., "Discovery of Estrogen Sulfotransferase Inhibitors from a Purine Library Screen," *J. Med. Chem.* 44:2683-2686 (2001); Armstrong et al., "Discovery of Carbohydrate Sulfotransferase Inhibitors from a Kinase-Directed Library," *Angewandte Chemie-International Edition* 39:1303-1306 (2000); Rosania et al., "Myoseverin, a Microtubule-Binding Molecule with Novel Cellular Effects," *Nature Biotech.* 18:304-308 (2000); Chang et al., "Synthesis and Application of Functionally diverse 2,6,9-Trisubstituted Purine Libraries as CDK Inhibitors," *Chem. & Biol.* 6:361-375 (1999); Gangjee et al., "Design, Synthesis, and Biological Activities of Classical N-[4-[2-(2-Amino-4-Ethylpyrrolo[2,3-d]Pyrimidin-5-yl)ethyl]benzoyl]-1-Glutamic Acid and its 6-Methyl Derivative as Potential Dual Inhibitors of Thymidylate Synthase and Dihydrofolate Reductase and as Potential Antitumor Agents," *J. Med. Chem.* 46:591-600 (2003); Baraldi et al., "Design, Synthesis, and Biological Evaluation of a Second Generation of Pyrazolo[4,3-e]-1,2,4-Triazolo[1,5-c]Pyrimidines as Potent and Selective A(2A) Adenosine Receptor Antagonists," *J. Med. Chem.* 41:2126-2133 (1998); and Baraldi et al., "7-Substituted 5-Amino-2-(2-furyl)Pyrazolo[4,3-e]-1,2,4-Triazolo[1,5-c]Pyrimidines as A(2A) Adenosine Receptor Antagonists: A Study on the Importance of Modifications at the Side Chain on the Activity and Solubility," *J. Med. Chem.* 45:115-126 (2002), which are hereby incorporated by reference in their entirety). The triazine scaffold has three-fold symmetry, and the positional modification is much more flexible than in the purines or pyrimidines. In a previous report, an orthogonal solid phase method to synthesize a triazine-based combinatorial library was described (Moon et al., "A Novel Microtubule Destabilizing Entity from Orthogonal Synthesis of Triazine Library and Zebrafish Embryo Screening," *J. Am. Chem. Soc.* 124:11608-11609 (2002); and Bork et al., "Novel Orthogonal Strategy Toward Solid-Phase Synthesis of 1,3,5-Substituted Triazines," *Org. Lett.* 5:117-120 (2003), which are hereby incorporated by reference in their entirety) and demonstrated anti-microtubule activities among the library entities (Schreiber, S. L., "The Small Molecule Approach to Biology," *Chem Eng News*, pp. 51-61 (2003), which is hereby incorporated by reference in its entirety). In addition, a similar chemistry has been applied to synthesize tagged linker libraries that were used to elucidate the first novel small molecule inhibitors for several ribosomal accessory proteins or their complex as the target (Nicolaou et al., "Handbook of Combinatorial Chemistry: Drugs, Catalysts, Materials," Wiley-VCH, Weinheim (2002), which is hereby incorporated by reference in its entirety). A similar chemistry to construct a novel hydrophobically capped linker triazine library, where three building blocks were prepared separately and assembled orthogonally to yield 1,120 highly pure compounds was applied in the present invention (FIG. 1). Each library compound contains a triethyleneglycol-benzoyl (TGBZ) linker at one of the diversity sites of the triazine scaffold. After biological screening, selected active compounds are re-synthesized in the free amine-linker form and attached to the affinity bead without the need for further laborious structure-activity relationship (SAR) work.

The present invention also relates to a method of treating a subject, including a human, with diabetes and obesity with a compound with the formula:

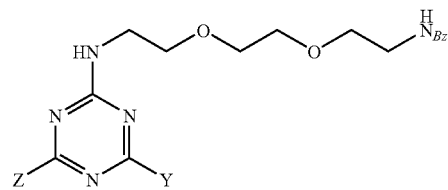

where Z is an amine, phenoxy, or thiol-containing group and Y is an alkyl-containing amine, under conditions effective to treat diabetes and obesity.

Pharmaceutical compositions according to the present invention can be administered by any convenient route, including parenterally, subcutaneously, intravenously, intramuscularly, intra peritoneally, or transdermally. Alternatively or concomitantly, administration may be by the oral route. The dosage administered depends upon the age, health, and weight of the recipient, nature of concurrent treatment, if any, and the nature of the effect desired.

Compositions within the scope of the present invention include all compositions wherein the active ingredient is contained in an amount effective to achieve its intended purpose. While individual needs vary, determination of optimal ranges of effective amounts of each compound is within the skill of the art. Typical dosages comprise 0.01 to 100 mg/kg body weight. The preferred dosages comprise 0.1 to 100 mg/kg body weight. The most preferred dosages comprise 1 to 50 mg/kg body weight.

Pharmaceutical compositions for administering the active ingredients of the present invention preferably contain, in addition to the pharmacologically active compound, suitable pharmaceutically acceptable carriers comprising excipients and auxiliaries which facilitate processing of the active compounds into preparations which can be used pharmaceutically. Preferably, the preparations, particularly those preparations which are administered orally and which can be used for the preferred type of administration, such as tablets, dragees, and capsules, and also preparations which can be administered rectally, such as suppositories, as well as suitable solutions for administration by injection or orally, contain from about 0.01 to about 99 percent by weight, preferably from about 20 to 75 percent by weight, active compound(s), together with the excipient. For purposes of the present invention, all percentages are by weight unless otherwise indicated. In addition to the following described pharmaceutical composition, the compounds of the present invention can be formulated as inclusion complexes, such as cyclodextrin inclusion complexes.

Examples of pharmaceutically acceptable acid addition salts for use in pharmaceutical compositions according to the present invention include those derived from mineral acids, such as hydrochloric, hydrobromic, phosphoric, metaphosphoric, nitric, and sulfuric acids, and organic acids such as tartaric, acetic, citric, malic, lactic, fumaric, benzoic, glycolic, gluconic, succinic, and arylsulfonic, such as p-toluenesulfonic, acids.

The pharmaceutically acceptable carriers include vehicles, adjuvants, excipients, or diluents that are well known to those skilled in the art and which are readily available. It is preferred that the pharmaceutically acceptable carrier be one which is chemically inert to the active compounds and which has no detrimental side effects or toxicity under the conditions of use.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste using, for example, maize starch, wheat starch, rice starch, potato starch, gelatin, tragacanth, methyl cellulose, hydroxypropylmethylcellulose, sodium carboxymethylcelullose, and/or polyvinyl pyrrolidone.

The active ingredients can be used as functionalized congeners for coupling to other molecules, such as amines and peptides. The use of such congeners provides for increased potency, prolonged duration of action, and prodrugs. Water solubility is also enhanced, which allows for reduction, if not complete elimination, of undesirable binding to plasma proteins and partition in to lipids. Accordingly, improved pharmacokinetics can be realized.

Another aspect of the present invention relates to a method of treating a subject for diabetes and obesity by treating the subject, including a human, with a compound which inhibits GAPDH under conditions necessary to treat diabetes and obesity. This method is carried out using the additives, doses, and modes of administration described above.

Another aspect of the present invention relates to a method of screening compounds which may be effective in modulating diabetes and obesity by providing a candidate compound and GAPDH, then contacting the candidate compound with the GAPDH under conditions effective to induce binding. Thus, the compound's potential effectiveness in modulating diabetes and obesity can be determined.

The triazine linker library molecules of the present invention can be used in a variety of phenotypic assays to find interesting small molecules and their binding proteins in an expeditious way. These assays can include Zebrafish embryo development, morphological changes in *S. pombe*, membrane potential sensing in cell systems, phenotypic screening in *C. elegans*, muscle regeneration in newt, tumorigenesis in brain cells, apoptosis and differentiation of cancer cells, cell migration and anti-angiogenesis. The active compounds are classified depending upon their ability to induce unique morphological changes, and these are then used for affinity matrix work.

The linker library molecules of the present invention can also be used for making a high density small molecule chip. Thousands of linker library molecules are immobilized on a glass slide by a spotting method, which can add hundreds to thousands of molecules to a slide. The amino end of the linker is connected to an activated functional group on the slide, such as isocyanate, isothiocyanate, or acyl imidazole. Fluorescent labeled proteins with different dyes are incubated with the slide. A scanner analyzes the color to give the absolute and relative binding affinity of different proteins on each compound. For example, no color means there is no activity with any kind of proteins. A strong mixed color means that the compounds are non-specifically active with multiple proteins. Exclusively stained compounds, with a single color, indicate selective binding of the relevant protein. Using this technique, thousands of small molecules can be tested in a short time using a small amount of protein. In this approach, limited numbers of purified proteins compete with each other in the presence of multiple small molecules. This approach is analogous to DNA microarray technology, which has been important in advances in functional genomics. Although there have been some reports of protein chips, at yet no small molecule library chip has been demonstrated. Therefore, the present invention may offer totally new techniques in the field of chemical genetics, which will expand the study of the entire genome.

Another aspect of the present invention relates to a method of screening compounds which may be effective in modulating diabetes and obesity by providing a candidate compound and *C. elegans* capable of transforming into a dauer state, then contacting the candidate compound with the *C. elegans*. The candidate compound which inhibits dauer formation is determined to be effective in modulating diabetes and obesity. Daf-2 is the only member of the insulin receptor family in the whole *C. elegans* genome sequence. Daf-2 is 36% identical to the insulin receptor and 35% identical to the IGF-1 receptor of human. The Daf-2 insulin-like signaling pathway controls *C. elegans* food intake, metabolism, growth and life span also. If there is a mutation in the Daf-2 insulin-like receptor, there is constitutive arrest at the dauer larval stage instead of growth to adulthood. Using this diabetic-like disease phenotype of a Daf-2 mutant, insulin sensitizers that activate downstream proteins of insulin-like signaling pathway can be screened. *C. elegans* is susceptible to the TGBz library of the present invention at a reasonable concentration. This fact, together with its simple culture and rapid life-cycle, make *C. elegans* ideal for new drug screening. *C. elegans* can be cultured in a simple aqueous solution in 96-well microtiter plates, allowing the relatively rapid screening of many hundreds of compounds.

The present invention dramatically accelerates chemical genetics techniques by connecting phenotypic assays and affinity matrix work without any delay, rather than requiring months to years of SAR work. This powerful technique will revolutionize the study of the genome and will open a new field of chemical proteomics. Combining the binding protein data with a phenotype index will serve as a general reference of chemical knock-out. The present invention makes it possible to identify novel protein targets for drug development as well as drug candidates. To identify the target protein, a free amino version of F43 derivative compound was immobilized on activated agarose affi-gel 10 beads with the remaining active functional groups on the resins blocked by ethanol amine. It was not necessary to study SAR to make this affinity matrix, because the pre-existing linker tag and the benzoyl group were simply exchanged with the agarose bead. Agarose beads treated only with ethanolamine were used as a negative control matrix. After incubation of these resins with *C. elegans* extract and washing with buffer, the bound proteins were directly digested on the resin by trypsin and the resulting peptides were analyzed by LC-MS 10. A total of twenty one proteins were identified from F43 resin and ten of them are overlapped with control resin.

EXAMPLES

The following examples are provided to illustrate embodiments of the present invention but are by no means intended to limit its scope.

Example 1

Synthesis of the TGBz Linker Library

FIG. 1 shows the general scheme for the synthesis of the TGBz linker library. The general scheme for orthogonal synthesis reagents and conditions is depicted: (a) TGBz linker (5 eq.), 2% acetic acid in THF, rt, 1 hr, followed by NaB(OAc)$_3$H (7 eq.), rt, 12 hrs. (b) Building block II (4 eq.) in THF 60° C., 1 hr., DIEA. (c) R$_2$R$_3$'NH, DIEA, NMP:n-BuOH=1:1, 120° C., 3 hrs. (d) 10% TFA in dichloromethane, 30 min.

First, 2,2'-(Ethylenedioxy)bis(ethylamine) (10 eq.) was dissolved in dichloromethane and the solution was cooled down to −78° C. in a dry ice/acetone bath. Benzoic anhydride (1 eq.) was dissolved in dichloromethane and added dropwise to the solution of 2,2'-(Ethylenedioxy)bis(ethylamine) over a period of 3 hours in a nitrogen gas atmosphere. The reaction mixture was allowed to stir for 10 hours followed by extraction with a saturated NaCl solution. The organic layers were combined and dried over MgSO$_4$. The solvent was removed in vacuo resulting in a 70% yield.

TGBz linker (2.8 mmole, 5 eq.) was added to a suspension of the PAL aldehyde resin (1.3 g, 1.43 mmole) in anhydrous tetrahydrofuran (THF) (50 ml containing 2% of acetic acid) at room temperature. The reaction mixture was shaken for 1 hr at room temperature followed by addition of sodium triacetoxyborohydride (2.1 g, 9.9 mmole, 7 eq.). The reaction mixture was stirred for 12 hrs. and filtered. The resin was washed with N,N-dimethylformamide (DMF) (5 times), alternatively with dichloromethane and methanol (MeOH) (5 times), and finally with dichloromethane (5 times). The resin was dried in a vacuum.

The general procedure for coupling of cyanuric trichloride to a variety of amines/anilines/alcohols was accomplished as follows. Cyanuric trichloride (1 equiv.) was dissolved in THF with DIEA (10 eq.) at 0° C. The desired amine/aniline (1.2 eq.) in THF was added dropwise. For addition of alcohols to cyanuric chloride, the same reaction conditions were followed except 2.5 eq. of K$_2$CO$_3$ was used instead of DIEA. The reaction mixture was stirred and monitored by TLC for 45 min. to 1 hour. A solid precipitate slowly formed. Upon completion of the reaction, the reaction mixture was quickly filtered through a plug of flash silica and washed with EA. The filtrate was evaporated in vacuo. The resulting products were purified using flash column chromatography (particle size 32-63 μm).

Building Block II (0.44 mmole) was added to Building Block I (0.11 mmole) in DIEA (1 ml.) and anhydrous THF (10 ml.) at room temperature. The reaction mixture was heated to 60° C. for 3 hrs. and filtered. The resin was washed with DMF (5 times), alternatively with dichloromethane and methanol (5 times), and finally dichloromethane (5 times). The resin was dried in a vacuum.

Desired amines (4 eq.) were added to the resin (10 mg), coupled with Building Block I and Building Block II, in DIEA (8 μl) and 1 ml of NMP: n BuOH (1:1). The reaction mixture was heated to 120° C. for 3 hrs. The resin was washed with DMF (5 times), alternatively with dichloromethane and methanol (5 times), and finally dichloromethane (5 times). The resin was dried in a vacuum. The product cleavage reaction was performed using 10% trifluoroacetic acid (TFA) in dichloromethane (1 ml) for 30 min. at room temperature and washed with dichloromethane (0.5 ml).

Free hydroxyl containing compounds were further treated with a piperazine resin in 0.5 ml THF at room temperature for 5 hrs. to cleave the trifluoroacetic ester that was formed upon treatment with TFA. The resin was filtered out and washed with 0.1 ml THF. The purity and identity of all the products were monitored by LC-MS at 250 nm (Agilent 1100 model). More than 90% of the compounds demonstrated >90% purity.

Example 2

*C. elegans* Growth and Assay

The Daf-2 mutant *C. elegans* strain e1370 was grown on nematode growth media (NGM) agar plates with *E. coli* (OP50) under standard conditions at 16° C. *C. elegans* mutant strains were obtained from the *Caenorhabditis* Genetics Center. Twenty synchronized early L2 animals grown at 16° C. were soaked in 96-well plates containing 100 μM of compounds/2% OP50 culture/M9 buffer, and then incubated at 25° C. for 4 days.

Worms (e1370) grown at 16° C. were harvested with extraction buffer [50 mM HEPES (pH 7.4), 150 mM NaCl, 2 mM EDTA] and washed twice with extraction buffer. Washed *C. elegans* pellets were re-suspended in 1 ml. of extraction buffer including a protease inhibitor cocktail (Sigma P8340) and then homogenized by intermittent sets of 10-15 strokes on ice using a Kontes 2 ml. tissue grinder (885303-0002). After adding Triton X-100 to a final concentration of 1%, the lysates were rotated for 15 min. at 4° C. and then cleared by centrifugation (14,000 rpm, 10 min.).

Figure 2:
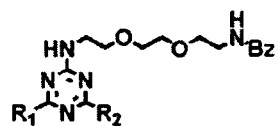
FIGS. 2A-F show various compounds (FIGS. 2A-C) and the effect of F43 on dauer formation in *C. elegans* larva.
Figure 2:
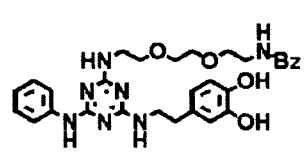
Figure 2:
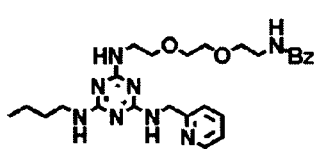
Figure 2:
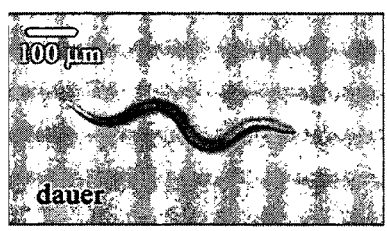
Figure 2:
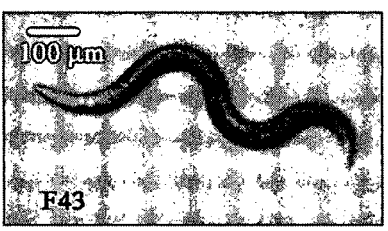
Figure 2:
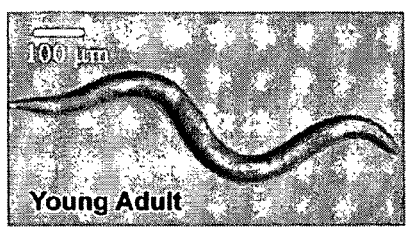

TG-Bz library (1120 members) compounds were screened in L2 stage worms grown at 16° C. by soaking in a 100 μM chemical solution and were warmed up to 25° C., in which 100% of untreated Daf-2 mutant larvae enter dauer within 24 hours. The TGBz compound F43 (FIG. 2B) was found to rescue larva from the dauer stage. E3 is the TGBz control compound (FIG. 2C). FIG. 2D shows a micrograph illustrating the thin body shape of *C. elegans* larva in the natural dauer state at 25° C. FIG. 2E shows the inhibition of the dauer state after treatment with 100 μM F43. It is apparent that F43 inhibits dauer formation as evidenced by the similar size of the larva to a *C. elegans* young adult.

Example 3

Glucose Uptake by 3T3-L1 Pre-Adipocytes

To validate the relevance of this *C. elegans* data to a mammalian system, F43 was tested for glucose uptake in 3T3-L1 pre-adipocytes using a fluorescent derivative of glucose, 2-NBD-deoxyglucose (Moon et al., "A Novel Microtubule Destabilizing Entity from Orthogonal Synthesis of Triazine Library and Zebrafish Embryo Screening," *J. Am. Chem. Soc.* 124:11608-11609 (2002), which is hereby incorporated by reference in its entirety).

3T3-L1 pre-adipocytes, were grown in DMEM (Dulbecco's Modified Eagle Medium Media) containing 1% antibiotics, and 10% heat-inactivated newborn calf serum under a humidified 5% CO$_2$ atmosphere. The cells were seeded in 48-well plates and allowed to adhere to the dish overnight. Cultures at 70-80% confluence were used for the chemical exposures. Cells were washed with PBS and pre-incubated in PBS for 5 min. 100 μM of 2-deoxy-NBD-glucose dissolved in PBS containing compounds were used to treat the cells for 15 min. at 37° C. (Leira et al., "Fluorescent Microplate Cell Assay to Measure Uptake and Metabolism of Glucose in Normal Human Lung Fibroblasts," *Toxicology in Vitro* 16:267-273 (2002), which is hereby incorporated by reference in its entirety). After washing with PBS, cells were lysed with 100 μl of 0.1 M potassium phosphate buffer (pH 10) containing 1% triton X-100 and then 50 μl of DMSO was added. Fluorescence intensity was measured in a fluorescence micro-plate reader at $\lambda_{ex}$=466 nm and $\lambda_{em}$=540 nm.

Figure 3:
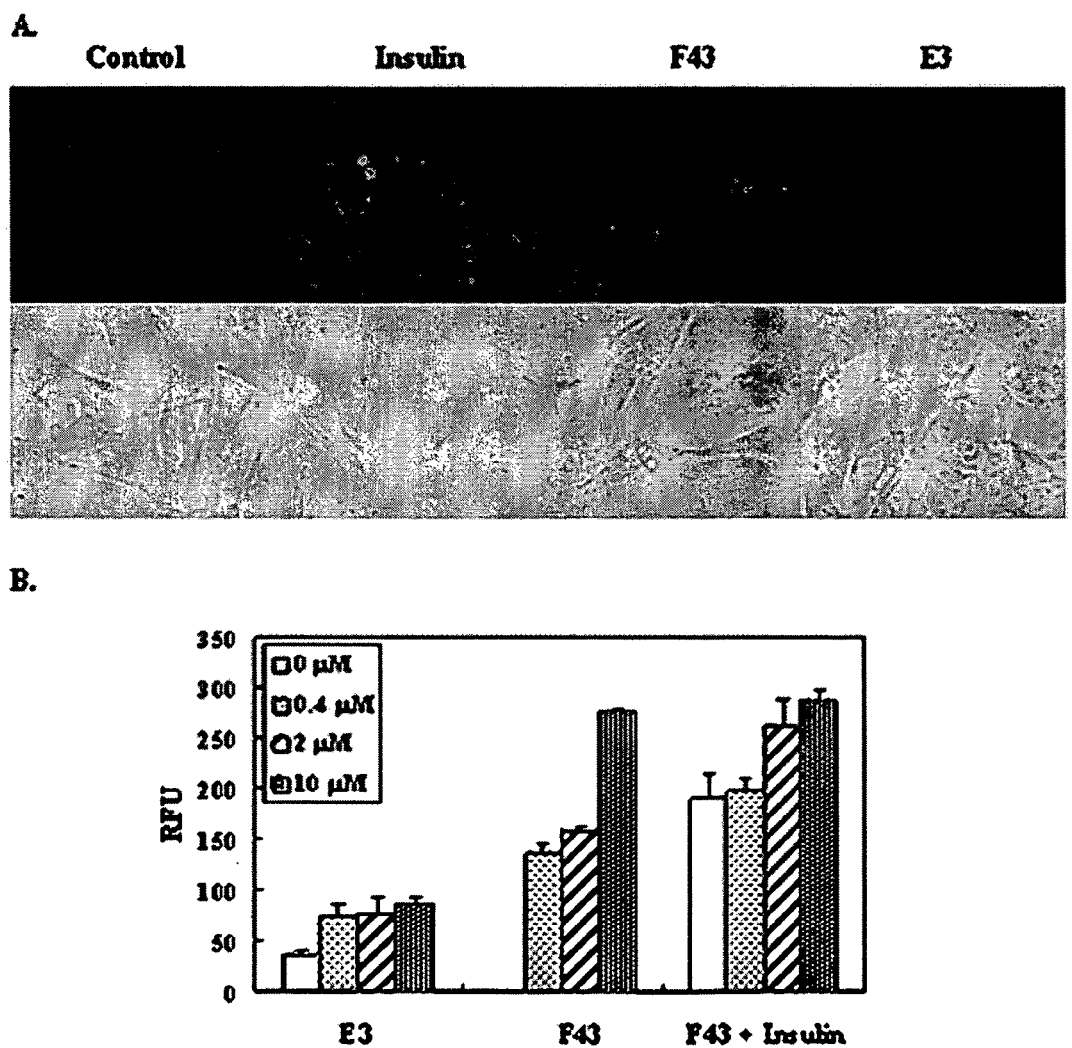
FIGS. 3A-B show the up-regulation of glucose uptake by 3T3-L1 pre-adipocytes upon treatment with Insulin, the TGBz compound F43, and the TGBz compound E3 as a control. The fluourescent dye 2-deoxy-NBD-glucose (2-NBDG) (100 uM) was used for visualization (FIG. 3A top panels). The bottom panels of FIG. 3A show unstained 3T3-L1 pre-adipocyte cells as seen by light microscopy.
Figure 4:
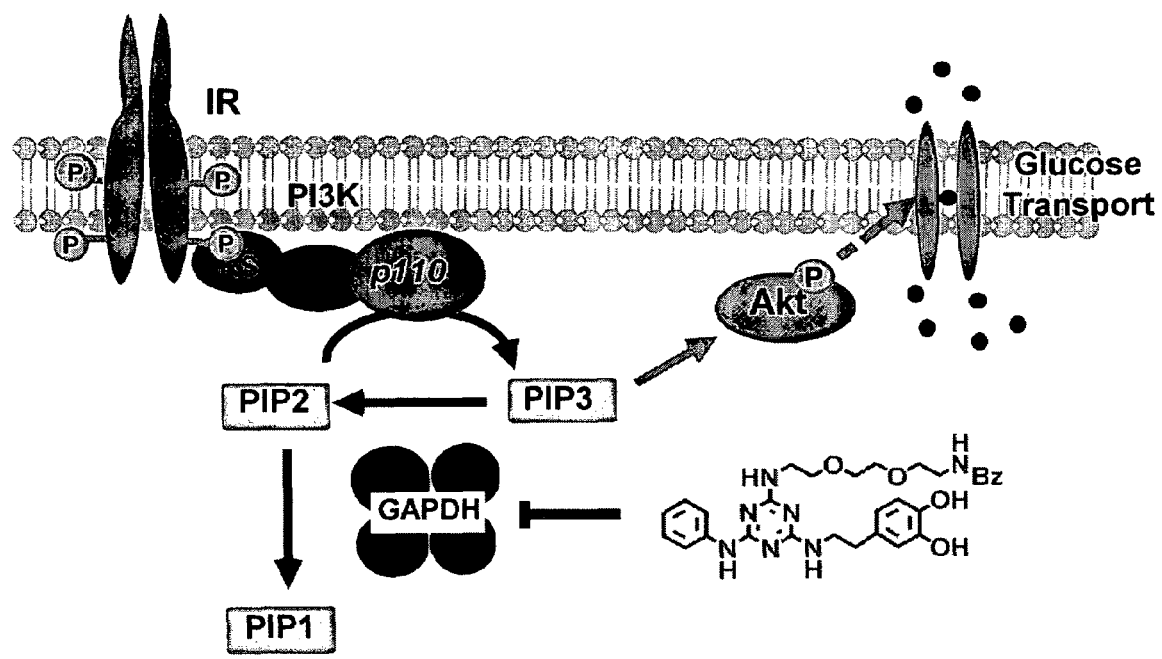
FIG. 4 shows a schematic representation of the intracellular signaling pathway showing where GAPDH acts and showing the putative binding site of TGBz compounds.

FIGS. 3A-B show the up-regulation of glucose uptake by 3T3-L1 pre-adipocytes upon treatment with Insulin, the TGBz compound F43, and the TGBz compound E3 as a control. The fluourescent dye 2-deoxy-NBD-glucose (2-NBDG) (100 uM) was used for visualization (FIG. 3A top panels). The bottom panels of FIG. 3A show cells through a bright field as controls, indicating that compound treatment was not toxic to pre-adipocyte cells. Five minutes before dye uptake, cells were incubated in PBS to diminish competition between 2-NBDG and glucose. Following incubation with the dye for 15 min. at 37° C., cells were washed with ice-cold PBS, and the fluorescence intensity was measured. The uptake of the fluorescent 2-NBDG was visualized by a Leica 2000 fluorescence microscope with excitation at 488 nm and long-pass detection at 530 nm and measured by a fluorescence microplate reader. The results are shown in FIG. 3B. The relative fluorescent units (RFU) are depicted on the y-axis. The concentrations of E3 (10 μM), F43 (10 μM), and the F43 (10 μM)/Insulin (100 nM) solution are shown. The error bars represent the range of four experiments.

Following incubation of F43 for 15 min., dose dependent glucose uptake was observed, while the control compound E3 did not show a clear increase (FIGS. 3A-B). Co-treatment of F43 with insulin (100 nM) demonstrated a synergistic effect, but at the highest concentration of F43 (10 μM), the glucose uptake effect was almost saturated (FIGS. 3A-B).

Example 4

Immobilization of Triazine Compounds onto Affigel-10 Gel beads and Affinity Matrix Production 0.5 ml (7.5 pmole) of Affigel-10 was transferred into a 3 ml cartridge with 20 μm pore size PE frit. The supernatant solvent was drained and affigel was washed with DMSO. A solution of 3.75 μmoles of a free-amine linker version of a TGBz compound in 0.5 ml DMSO and 50 μl DIEA were added to the gel. The solution was agitated for 3 hrs. at room temperature. The resulting slurry was drained and the gel was washed with DMSO. The loading level (90%) was determined by analyzing the eluent mixed with internal standard by LCMS and comparing the result to the initial reaction mixture. A solution of 50 mM ethanolamine solution in 1 ml of DMSO and 15 μl DIEA was added to the reaction cartridge. The solution was agitated for 3 hrs. at room temperature. The resulting slurry was drained and the gel was washed with DMSO, water, and 2% sodium azide in water. The affigel product was stored in 2% sodium azide solution in water (1 ml) at 4° C.

For the production of the affinity matrix, 50 μl of packed beads were washed three times with 1 ml of bead buffer [50 mM HEPES (pH 7.4), 250 mM NaCl, 5 mM EDTA, protease inhibitor cocktail tablets (Roche, Cat No. 1 697 498) 1 tablet for 50 ml. The bead was re-suspended in 150 μl of this buffer and then an equal volume of the protein extract was added to the bead suspension; the tubes were shaken at 4° C. for 1 hr. After removing the supernatant by centrifugation at 10,000 rpm for 3 min. at 4° C., the beads were washed 7 times with 1 ml of bead buffer. Protein identification by mass spectrometry was performed as described (Cheeseman et al., "Implication of a Novel Multiprotein Dam1p Complex in Outer Kinetochore Function," *J Cell Biol* 155:1137-45 (2001), which is hereby incorporated by reference in its entirety).

To identify the target protein, a free amino version of an F43 derivative compound was immobilized on activated agarose affi-gel 10 beads, and leftover active functional groups on the resins were blocked by ethanol amine. It is noteworthy that there was no need for a SAR study to make this affinity matrix thanks to the pre-existing linker tag, and the benzoyl group was simply exchanged with the agarose bead. Ethanolamine-only treated agarose beads were used as a negative control matrix. After incubation of these resins with *C. elegans* extract and washing with buffer, the bound proteins were analyzed by SDS gel, but no distinguishable bands appeared with a serious smearing. Thus, the whole bound proteins were directly digested on the resin by trypsin and the resulting peptides were analyzed by LC-MS (Cheeseman et al., "Implication of a Novel Multiprotein Dam1p Complex in Outer Kinetochore Function," *J Cell Biol* 155:1137-45 (2001), which is hereby incorporated by reference in its entirety). Twenty one proteins were identified from F43 resin and ten of them overlapped with control resin, as shown in Table 3 below.

TABLE 3

| Wormpep | Description |
| --- | --- |
| F43 affinity matrix only | |
| H28O16.1a | ATP synthase alpha and beta subunits |
| 46F11.2 | *C. Elegans* Y-box |
| F25H5.4 | elongation factor Tu family |
| T21B10.2a | Enolase |
| K109B3.8 | GAPDH |
| FD2096.8 | nucleosome assembly protein |
| R11A5.4a | phosphoenolpyruvate carboxykinase |
| Y24D9A.4 | ribosomal protein L7Ae/L30e/S12e/Gadd45 |
| K02F2.2 | S-adenosylhomocysteine hydrolase |
| FC36E8.5 | tubulin beta-4q chain |
| F26E4.8 | tubulin, alpha |
| Overlap with control affinity matrix | |
| F42C5.8 | 40S ribosomal protein S8 |
| C09D4.5 | 60S ribosomal protein L19 |
| F13B10.2a | 60S ribosomal protein L3 |
| B0041.4 | ribosomal protein L1 |
| JC8.3a | ribosomal protein L11 |
| T04C12.5 | Actin |
| F46H5.3a | arginine kinase |
| C34E10.6 | ATP synthase beta chain |
| R03G5.1a | elongation factor EF-1-alpha |
| K07H8.6a | Vitellogenin |
| Control affinity matrix only | |
| B0393.1 | 40S ribosomal protein |
| T08B2.10 | 40S ribosomal protein S17 |
| F11C3.3 | myosin heavy chain |

Example 5

RNA Interference Assay

To identify the real target out of these F43-selective binding proteins, RNA interference was tested against all the candidates. Bacteria containing clones for RNAi were spotted in each NGM agar plate containing 6 mM IPTG and 50 μg/ml ampicillin. To synchronize, 40 gravid adult worms were placed in duplicate plates (for 2 hrs. at 16° C.), and then removed (generally 200-250 eggs per plate). After a 36 hr. incubation at 16° C., one set of the plates was transferred to 25° C. to induce dauer formation, and another set of the plates were continuously incubated at 16° C. as a control for normal growth. Phenotypic change was monitored for 4 days. From a total of 11 target proteins tested by RNAi, one of them inhibited dauer formation. For GAPDH (K10B3.8), the clone encoding GAPDH, the ratio of inhibiting dauer formation is 3.6% out of 250 worms.

Example 6

In Vitro GAPDH Inhibition Assay

Figure 7:
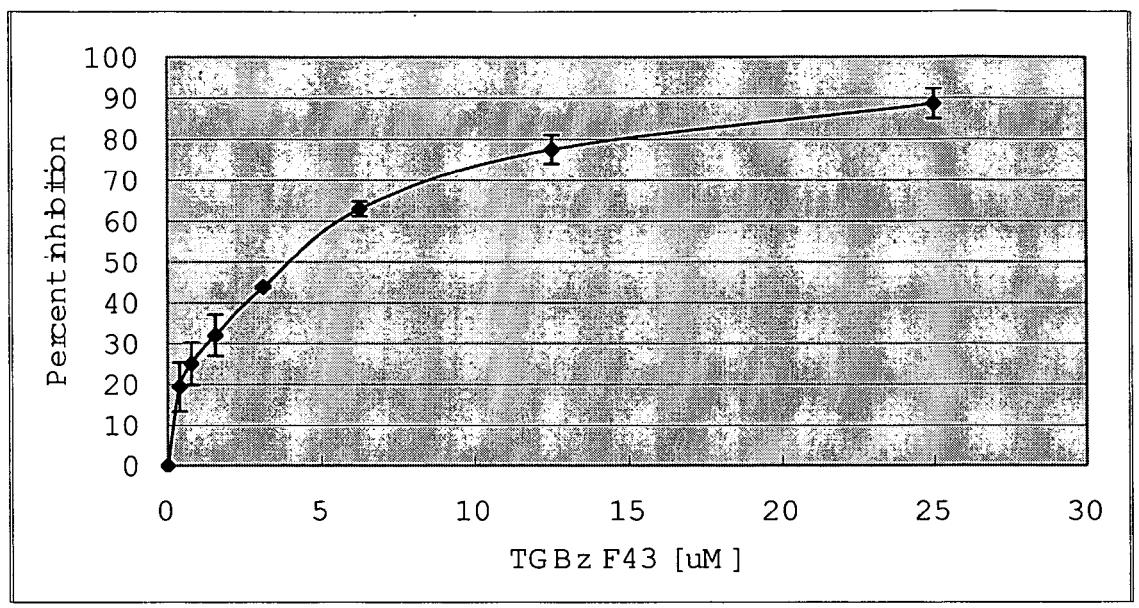
FIG. 7 shows the activity of F43 against GAPDH. GAPDH inhibition activity was measured by monitoring the amount of NADH produced by a fluorescence plate reader at $\lambda_{ex}=340$ nm, $\lambda_{em}=460$ nm (ex=excitation, em=emission wave length).

To confirm the activity of F43 against GAPDH, rabbit muscle GAPDH was tested in vitro by showing the $IC_{50}$ of F43 was 4 µM, whereas the control compound E3 was higher than 100 µM. GAPDH inhibition activity was measured fluorometrically as previously described (Byers, L. D., "Glyceraldehyde-3-Phosphate Dehydrogenase from Yeast," *Methods in Enzymology* 89:326-335 (1982), which is hereby incorporated by reference in its entirety). Rabbit muscle GAPDH and glyceraldehydes-3-phosphate (GAP) were employed. The assay was performed in black polypropylene 96-well microtiter plates using a 100 µl solution of 100 mM sodium phosphate at pH 8.6, 5 mM EDTA, 0.2 mM GAP, 0.1 mM $NAD^+$, 0.5 units of GAPDH in the presence of varying concentrations of compound. The reaction was initiated by addition of GAP. Amounts of produced NADH was monitored by a fluorescence plate reader, at $\lambda_{ex}$=340 nm, $\lambda_{em}$=460 nm (ex=excitation, em=emission wave length) (FIG. 7).

Activation of insulin receptor leads to activation of other signaling molecules such as phosphoinositide-3-OH kinase (PI3-K) and their downstream effectors, such as Akt (Phospho-kinase B). The kinase cascades in turn regulating glucose transporter localization, and the transcription and translation of genes related growth and proliferation. GAPDH was identified as the target protein of the active compound. This leads to a working hypothesis that GAPDH, the highly abundant house keeping protein, constitutively suppresses the insulin signaling pathway as a phosphatase. If F43 inhibits the GAPDH, the originally constrained insulin signaling is released to effect downstream activation, resulting in glucose uptake.

In summary, the present invention provides a tagged library approach for insulin mimetic compound discovery using a method of inhibiting dauer formation of Daf-2 mutants in a forward chemical genetics format. As a result, GAPDH was identified as the target protein of the active compound, thus GAPDH, the highly abundant house keeping protein, likely constitutively suppresses the insulin signaling pathway. If F43 inhibits GAPDH, the originally constrained insulin signaling is released to activate the down stream events and at least one of the end results is glucose uptake. While GAPDH has long been recognized as playing a key role in glycolysis, recent studies have shown additional functions of the old protein including uracil DNA glycosylase, transcription activation, nuclear RNA export, DNA repair and also kinase/phosphatase activity (Sirover, M. A., "New Insights into an Old Protein: the Functional Diversity of Mammalian Glyceraldehyde-3-Phosphate Dehydrogenase," *Biochim Biophys Acta* 1432:159-84 (1999); and Sirover, M. A., "New Insights into an Old Protein: The Functional Diversity of Mammalian Glyceraldehyde-3-Phosphate Dehydrogenase," *Biochimica Et Biophysica Acta-Protein Structure and Molecular Enzymology* 1432:159-184 (1999), which are hereby incorporated by reference in their entirety). The present invention elucidates another function of GAPDH as an active regulator of glucose transport via a previously known insulin pathway and casts light on GAPDH as a novel target for diabetes and obesity studies.

Although the invention has been described in detail for the purposes of illustration, it is understood that such detail is solely for that purpose, and variations can be made therein by those skilled in the art without departing from the spirit and scope of the invention as defined in the claims that follow.

What is claimed is:

1. A compound having the following formula:

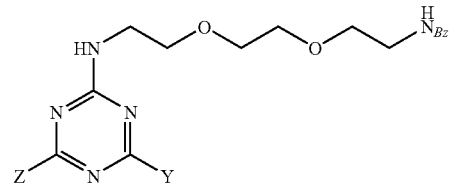

wherein

Z is an amine, phenoxy, or thiol-containing group; and
Y is an alkyl-containing amine.

2. The compound of claim 1, wherein
Z has a structure selected from the group consisting of

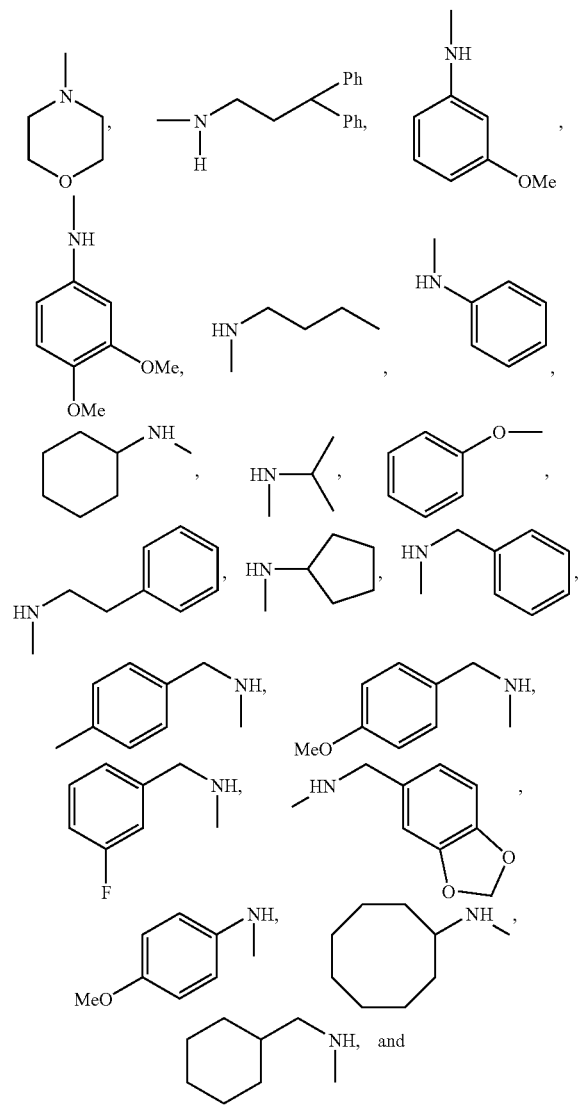

-continued
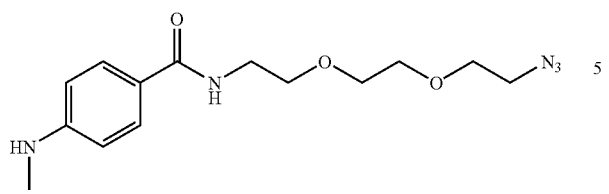
and
Y has a structure selected from the group consisting of
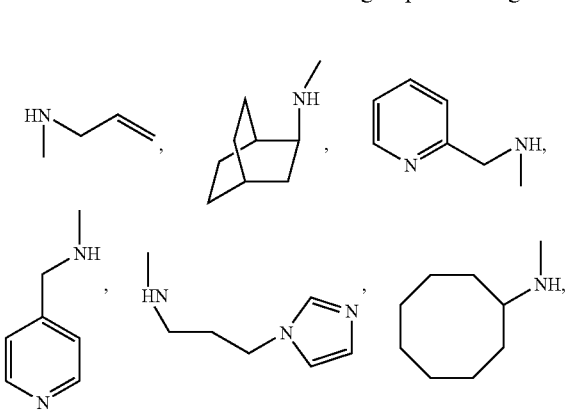
-continued
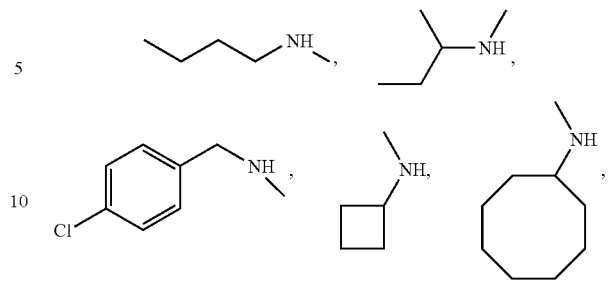

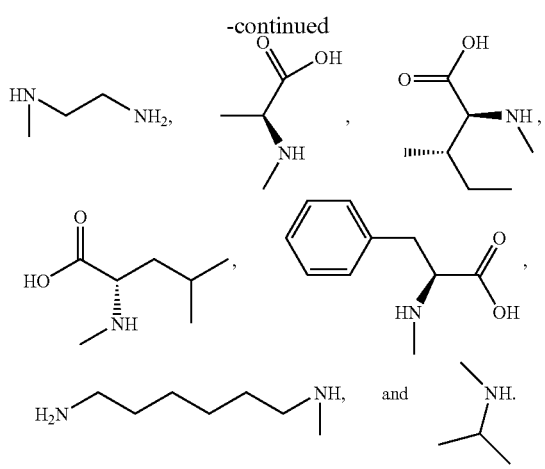

3. The compound of claim 1, wherein the compound has the following formula:

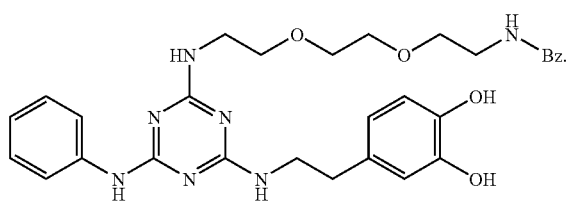

4. A process for synthesizing a product compound having the following formula:

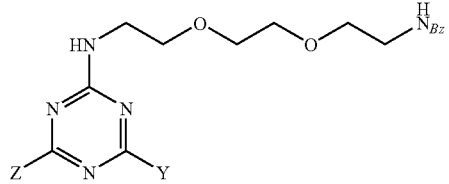

wherein
  Z is an amine, phenoxy, or thiol-containing group, and
  Y is an alkyl-containing amine,
said process comprising:
  providing an immobilized precursor compound of the following formula:

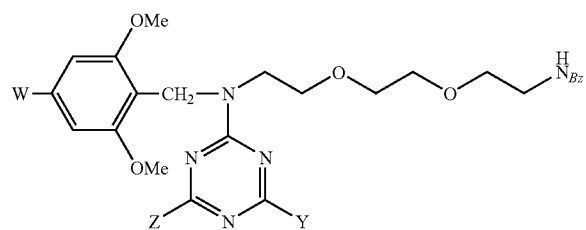

wherein
  W is a solid support; and
  converting the immobilized precursor compound to the product compound.

5. The process of claim 4, wherein
Z has a structure selected from the group consisting of

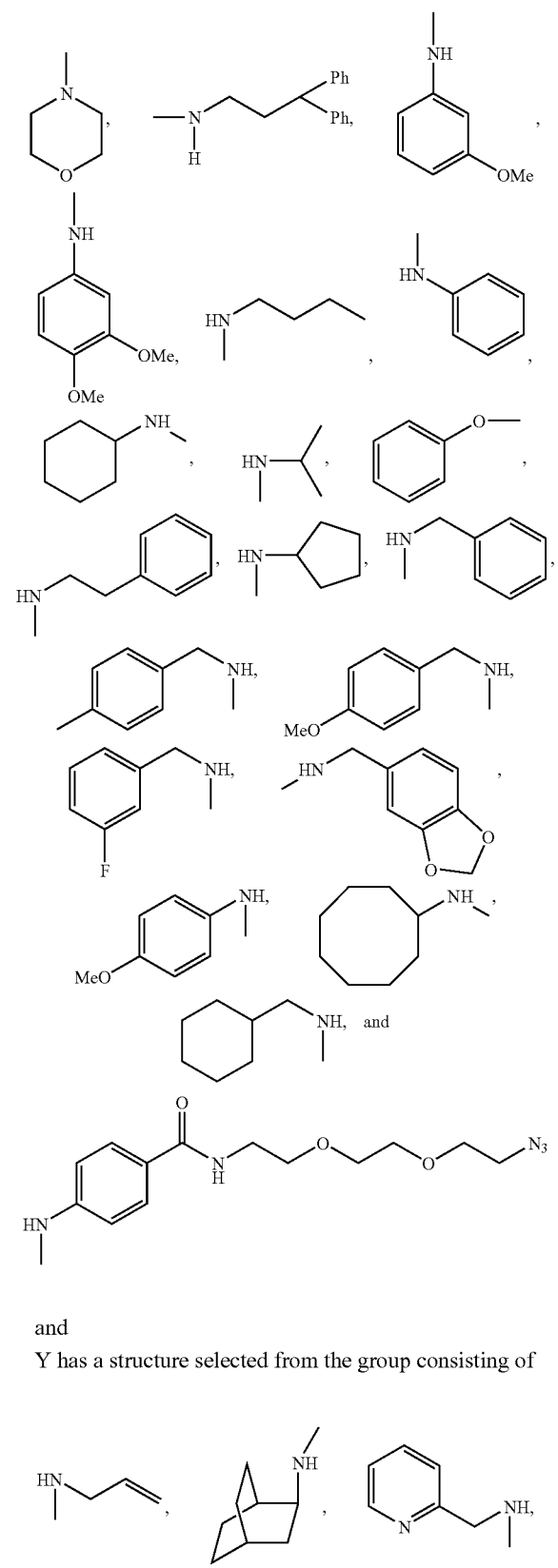

and
Y has a structure selected from the group consisting of

-continued
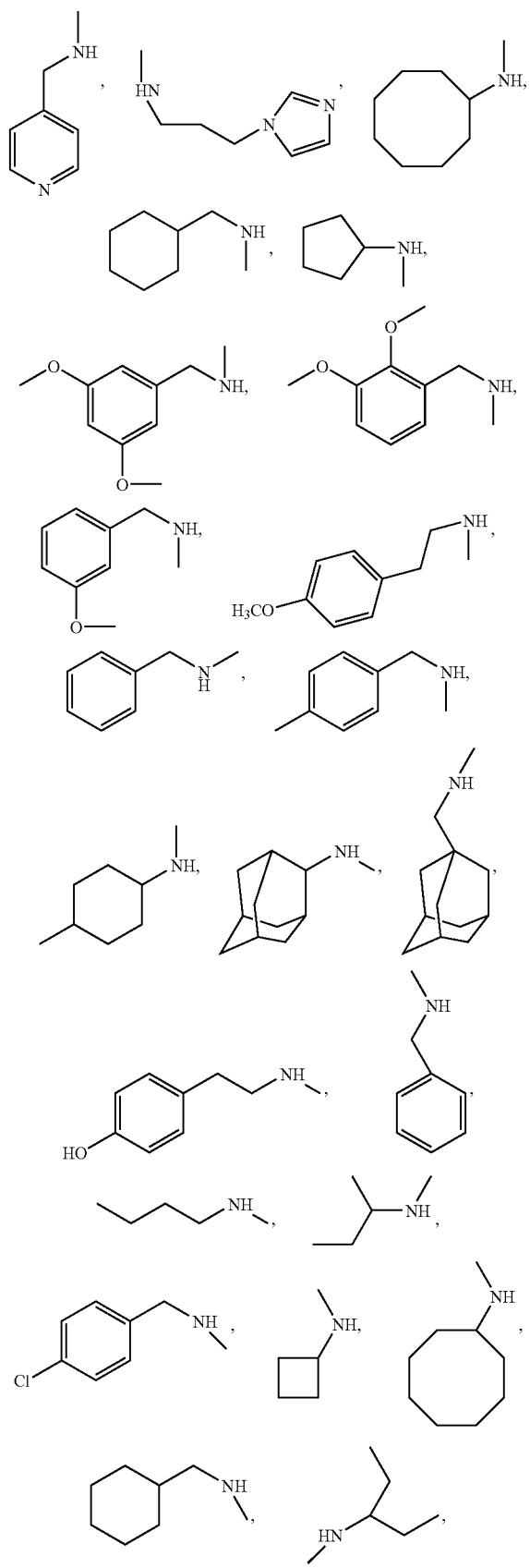
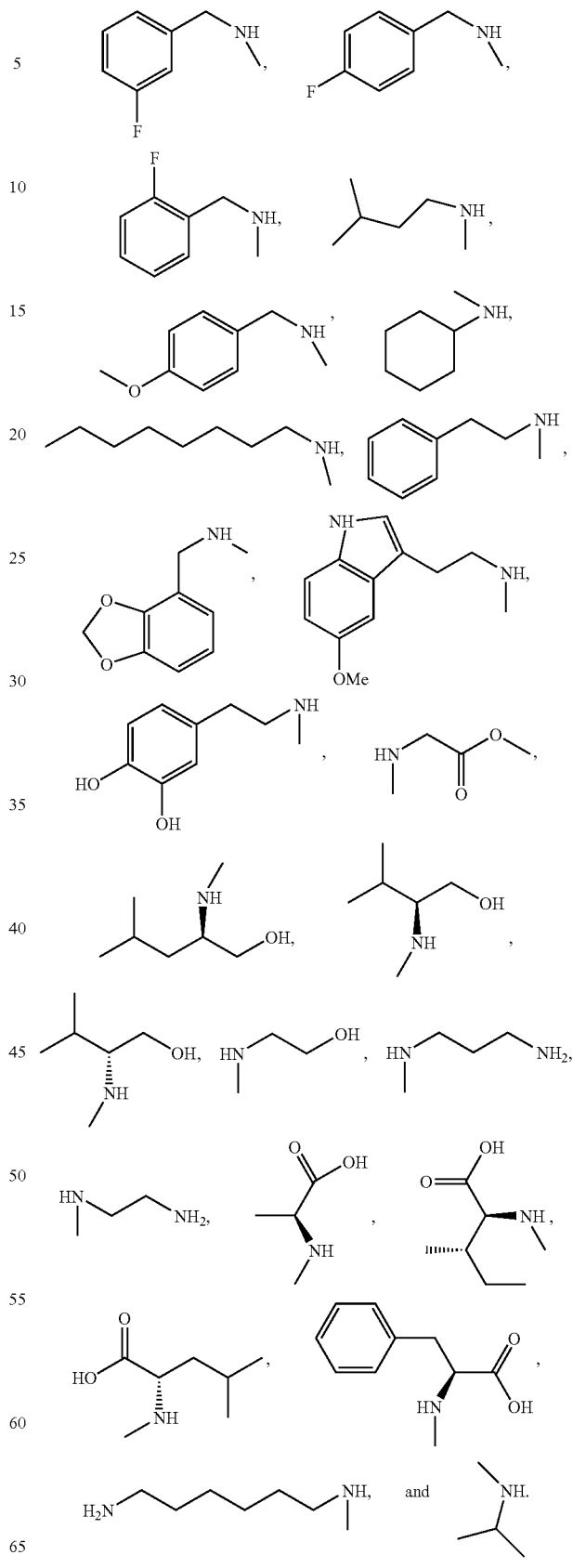

6. The process of claim 4, wherein the product compound has the following formula:

[chemical structure]

7. The process of claim 4, wherein providing the immobilized precursor compound comprises:
providing a first intermediate compound of the formula:

Y—H;

providing an immobilized intermediate compound of the formula:

[chemical structure]

and
reacting the first intermediate compound with the immobilized intermediate compound under conditions effective to form the immobilized precursor compound.

8. The process of claim 7, wherein said providing the immobilized intermediate compound comprises:
providing a secondary intermediate compound of the formula:

[chemical structure]

providing a secondary immobilized intermediate compound of the formula:

[chemical structure]

and
reacting the secondary intermediate compound and the secondary immobilized intermediate compound under conditions effective to produce the immobilized intermediate compound.

9. The process of claim 8, wherein said providing the secondary intermediate compound comprises:
reacting a first starting compound of the formula:

[chemical structure]

with a second starting compound of the formula:

Z-H under conditions effective to produce the secondary intermediate compound.

10. The process of claim 8, wherein said providing a secondary immobilized intermediate compound comprises:
converting an immobilized reactant compound of the formula:

[chemical structure]

under conditions effective to produce the secondary immobilized intermediate compound.

11. A compound having the following formula:

[chemical structure]

wherein
Z is an amine, phenoxy, or thiol-containing group; and
Y has a structure selected from the group consisting of

[chemical structures]

12. The compound of claim 11, wherein
Z has a structure selected from the group consisting of

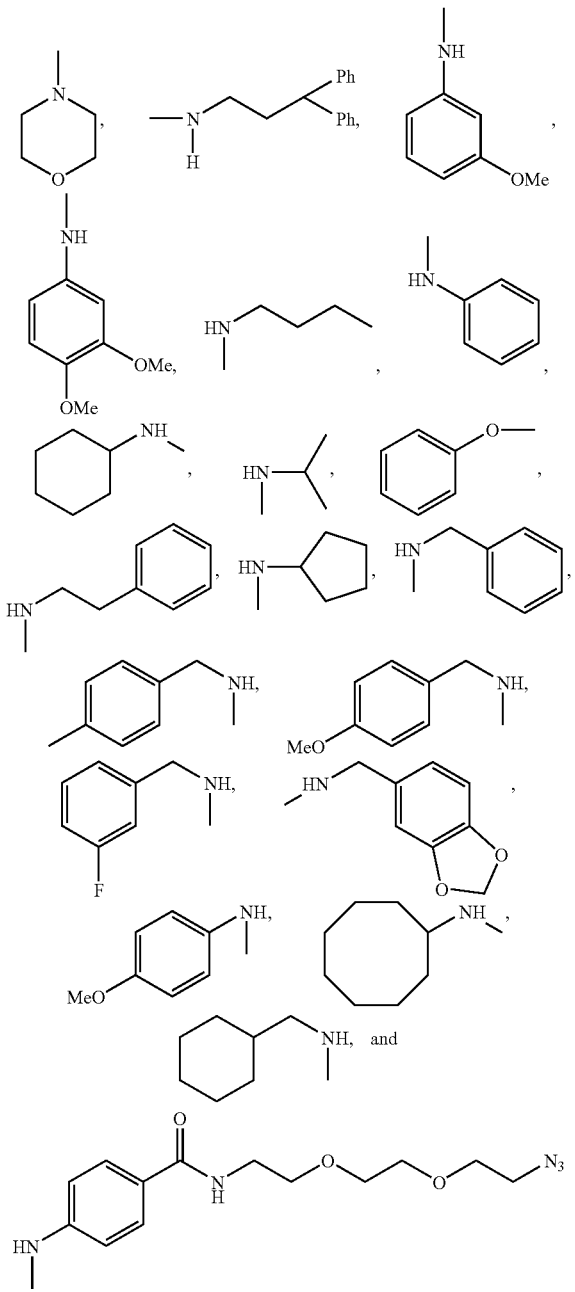

13. A process for synthesizing a product compound having the following formula:

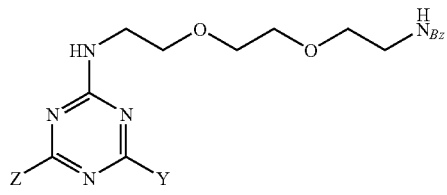

wherein
Z is an amine, phenoxy, or thiol-containing group, and
Y is selected from the group consisting of

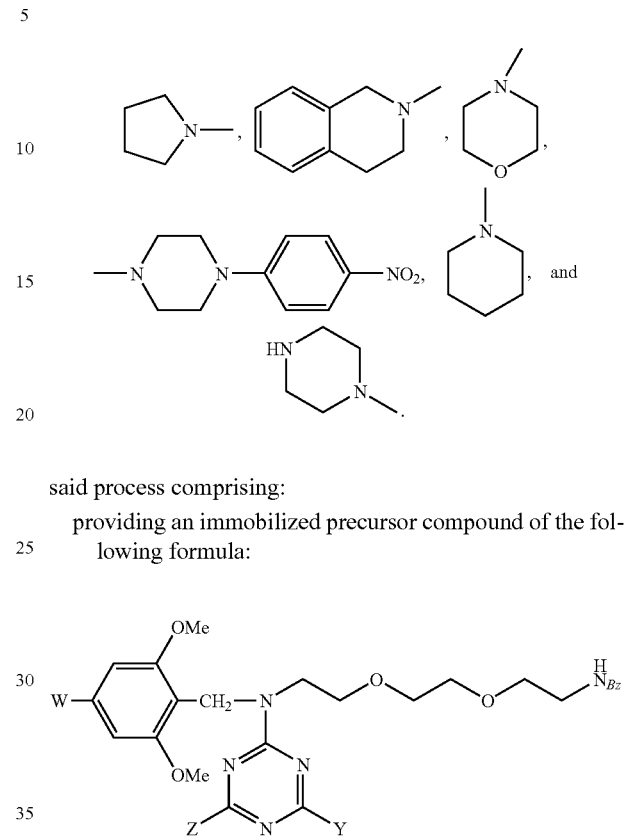

said process comprising:
providing an immobilized precursor compound of the following formula:

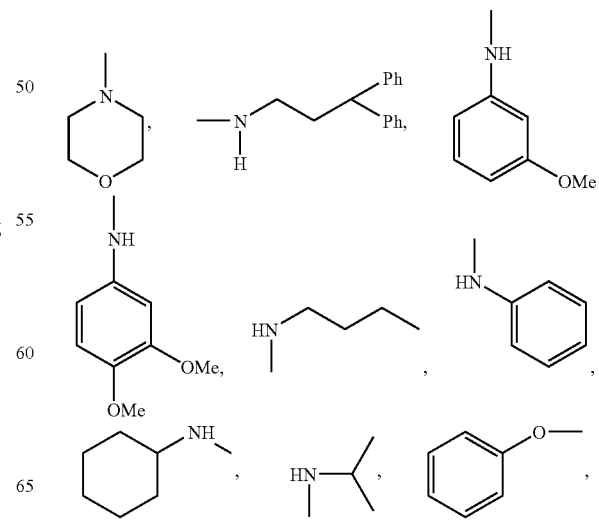

wherein
W is a solid support; and
converting the immobilized precursor compound to the product compound.

14. The process of claim 13, wherein
Z has a structure selected from the group consisting of -continued

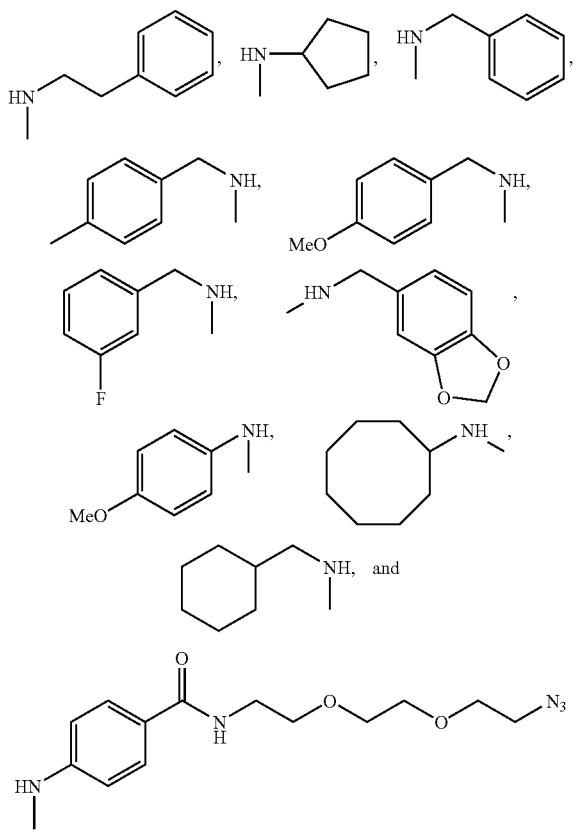

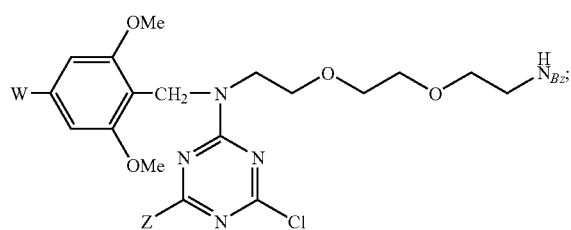

15. The process of claim 13, wherein providing the immobilized precursor compound comprises:

providing a first intermediate compound of the formula:

Y—H;

providing an immobilized intermediate compound of the formula:

and
reacting the first intermediate compound with the immobilized intermediate compound under conditions effective to form the immobilized precursor compound.

16. The process of claim 15, wherein said providing the immobilized intermediate compound comprises:

providing a secondary intermediate compound of the formula:

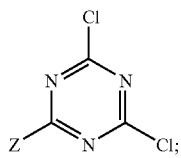

providing a secondary immobilized intermediate compound of the formula:

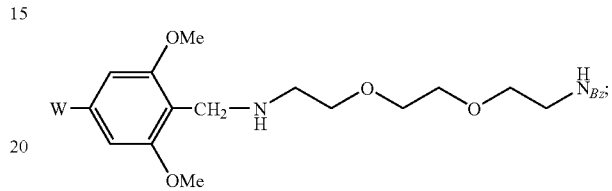

and
reacting the secondary intermediate compound and the secondary immobilized intermediate compound under conditions effective to produce the immobilized intermediate compound.

17. The process of claim 16, wherein said providing the secondary intermediate compound comprises:

reacting a first starting compound of the formula:

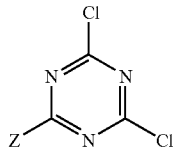

with a second starting compound of the formula:

Z-H under conditions effective to produce the secondary intermediate compound.

18. The process of claim 16, wherein said providing a secondary immobilized intermediate compound comprises:

converting an immobilized reactant compound of the formula:

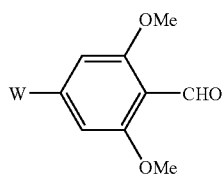

under conditions effective to produce the secondary immobilized intermediate compound.

* * * * *